US010842624B2

(12) United States Patent
Perszyk et al.

(10) Patent No.: US 10,842,624 B2
(45) Date of Patent: Nov. 24, 2020

(54) TRANSSEPTAL MITRAL VALVE DELIVERY SYSTEM

(71) Applicant: St. Jude Medical, Cardiology Division, Inc., St. Paul, MN (US)

(72) Inventors: Brian Joseph Perszyk, Shoreview, MN (US); Mathias Charles Glimsdale, St. Michael, MN (US); Theodore Paul Dale, Corcoran, MN (US); Justin Herbert, Champlin, MN (US); Christopher William Hunt, Elk River, MN (US); Bryan Cheng Yang Goh, Brooklyn Park, MN (US); Natasha Louise Bond, Louisville, CO (US); Ross David Paulson, Ramsey, MN (US); Bryan Clare Patrick, Brooklyn Park, MN (US); Benedict Skemp, St. Louis Park, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 260 days.

(21) Appl. No.: 15/915,196

(22) Filed: Mar. 8, 2018

(65) Prior Publication Data
US 2018/0256327 A1    Sep. 13, 2018

Related U.S. Application Data

(60) Provisional application No. 62/469,646, filed on Mar. 10, 2017.

(51) Int. Cl.
*A61F 2/95* (2013.01)
*A61F 2/24* (2006.01)

(52) U.S. Cl.
CPC .......... *A61F 2/2436* (2013.01); *A61F 2/2418* (2013.01); *A61F 2/2439* (2013.01); *A61F 2/2412* (2013.01); *A61F 2/9517* (2020.05)

(58) Field of Classification Search
CPC .... A61F 2/2436; A61F 2/2418; A61F 2/2439; A61F 2/2412; A61F 2002/9517; A61F 2/962
See application file for complete search history.

(56) References Cited

U.S. PATENT DOCUMENTS

| 3,657,744 A | 4/1972 | Ersek |
| 4,423,730 A | 1/1984 | Gabbay |

(Continued)

FOREIGN PATENT DOCUMENTS

| DE | 102005003632 A1 | 8/2006 |
| DE | 202010007592 U1 | 10/2010 |

(Continued)

OTHER PUBLICATIONS

International Search Report including Written Opinion for PCT/US2018/021438 dated May 22, 2018.

(Continued)

*Primary Examiner* — Jing Rui Ou
(74) *Attorney, Agent, or Firm* — Lerner, David, Littenberg, Krumholz & Mentlik, LLP

(57) ABSTRACT

A delivery device for a prosthetic mitral valve includes five sheaths and a handle. The first sheath is coupled to a first handle portion and is rotatable and bendable. The second sheath is coupled to a second handle portion and extends through the first sheath. The second sheath is bendable, rotatable and translatable relative to the first sheath. The third sheath is coupled to a third handle portion and extends through the first and second sheaths. The third sheath is translatable relative to the second sheath. The second handle portion is coupled to the first and third handle portions. The fourth sheath extends through the third sheath and forms part of a compartment to store the prosthetic valve. The fifth sheath extends through the fourth sheath to a tip and is (Continued)

coupled to a retaining sheath that closes the compartment to retain the valve in a collapsed condition.

18 Claims, 26 Drawing Sheets

(56) References Cited

U.S. PATENT DOCUMENTS

| | | | |
|---|---|---|---|
| 5,078,720 | A | 1/1992 | Burton et al. |
| 5,415,664 | A | 5/1995 | Pinchuk |
| 5,484,444 | A | 1/1996 | Braunschweiler et al. |
| 5,571,168 | A * | 11/1996 | Toro ............... A61F 2/95 623/1.11 |
| 5,702,418 | A | 12/1997 | Ravenscroft |
| 5,824,041 | A | 10/1998 | Lenker et al. |
| 5,843,167 | A | 12/1998 | Dwyer et al. |
| 5,924,424 | A | 7/1999 | Stevens et al. |
| 5,968,068 | A | 10/1999 | Dehdashtian et al. |
| 5,980,533 | A | 11/1999 | Holman |
| 6,077,297 | A | 6/2000 | Robinson et al. |
| 6,139,572 | A * | 10/2000 | Campbell ............... A61F 2/958 623/1.1 |
| 6,269,819 | B1 | 8/2001 | Oz et al. |
| 6,306,141 | B1 | 10/2001 | Jervis |
| 6,391,050 | B1 | 5/2002 | Broome |
| 6,468,299 | B2 | 10/2002 | Stack et al. |
| 6,623,518 | B2 | 9/2003 | Thompson et al. |
| 6,814,746 | B2 | 11/2004 | Thompson et al. |
| 6,830,584 | B1 | 12/2004 | Seguin |
| 7,018,406 | B2 | 3/2006 | Seguin et al. |
| 7,022,133 | B2 * | 4/2006 | Yee ............... A61M 25/00 623/1.11 |
| 7,311,730 | B2 | 12/2007 | Gabbay |
| 7,510,572 | B2 | 3/2009 | Gabbay |
| 7,682,390 | B2 | 3/2010 | Seguin |
| 7,803,185 | B2 | 9/2010 | Gabbay |
| 8,840,663 | B2 | 9/2014 | Salahieh et al. |
| 2003/0050694 | A1 | 3/2003 | Yang et al. |
| 2004/0210304 | A1 | 10/2004 | Seguin et al. |
| 2005/0137695 | A1 | 6/2005 | Salahieh et al. |
| 2005/0137697 | A1 | 6/2005 | Salahieh et al. |
| 2005/0240200 | A1 | 10/2005 | Bergheim |
| 2006/0074484 | A1 | 4/2006 | Huber |
| 2006/0106415 | A1 | 5/2006 | Gabbay |
| 2006/0142848 | A1 | 6/2006 | Gabbay |
| 2006/0167468 | A1 | 7/2006 | Gabbay |
| 2006/0259120 | A1 | 11/2006 | Vongphakdy et al. |
| 2007/0010876 | A1 | 1/2007 | Salahieh et al. |
| 2007/0027534 | A1 | 2/2007 | Bergheim et al. |
| 2007/0043435 | A1 | 2/2007 | Seguin et al. |
| 2007/0055358 | A1 | 3/2007 | Krolik et al. |
| 2007/0073391 | A1 | 3/2007 | Bourang et al. |
| 2007/0088431 | A1 | 4/2007 | Bourang et al. |
| 2007/0112422 | A1 | 5/2007 | Dehdashtian |
| 2007/0162100 | A1 | 7/2007 | Gabbay |
| 2007/0168013 | A1 | 7/2007 | Douglas |
| 2007/0203575 | A1 | 8/2007 | Forster et al. |
| 2007/0239271 | A1 | 10/2007 | Nguyen |
| 2007/0244552 | A1 | 10/2007 | Salahieh et al. |
| 2008/0071369 | A1 | 3/2008 | Tuval et al. |
| 2008/0147182 | A1 | 6/2008 | Righini et al. |
| 2009/0054975 | A1 | 2/2009 | del Nido et al. |
| 2010/0004740 | A1 | 1/2010 | Seguin et al. |
| 2010/0191326 | A1 * | 7/2010 | Alkhatib ............... A61F 2/2439 623/2.11 |
| 2010/0286768 | A1 | 11/2010 | Alkhatib |
| 2010/0298931 | A1 | 11/2010 | Quadri et al. |
| 2011/0054586 | A1 * | 3/2011 | Mayberry ............... A61F 2/966 623/1.11 |
| 2011/0224678 | A1 | 9/2011 | Gabbay |
| 2014/0309680 | A1 * | 10/2014 | Fargahi ............... A61F 2/95 606/191 |
| 2015/0250481 | A1 * | 9/2015 | Chobotov ............... A61F 2/954 623/1.12 |
| 2016/0045311 | A1 | 2/2016 | McCann et al. |
| 2016/0113766 | A1 * | 4/2016 | Ganesan ............... A61F 2/2412 623/2.11 |
| 2017/0325945 | A1 | 11/2017 | Dale et al. |

FOREIGN PATENT DOCUMENTS

| | | |
|---|---|---|
| EP | 1129744 A1 | 9/2001 |
| EP | 1157673 A2 | 11/2001 |
| EP | 1926455 A2 | 6/2008 |
| WO | 02067782 A2 | 9/2002 |
| WO | 07071436 A2 | 6/2007 |
| WO | 08070797 A2 | 6/2008 |
| WO | 2010051025 A1 | 5/2010 |
| WO | 2010087975 A1 | 8/2010 |
| WO | 2013171007 A1 | 11/2013 |
| WO | 2015036617 A2 | 3/2015 |

OTHER PUBLICATIONS

Quaden et al., "Percutaneous aortic valve replacement: resection before implantation", European J. of Cardio-thoracic Surgery, vol. 27, Issue 5, pp. 836-840, May 2005.

Ruiz, "Overview of PRE-CE Mark Transcatheter Aortic Valve Technologies", Euro PCR, dated May 25, 2010.

* cited by examiner

TRANSSEPTAL MITRAL VALVE DELIVERY SYSTEM

CROSS-REFERENCE TO RELATED APPLICATIONS

This application claims the benefit of the filing date of U.S. Provisional Patent Application No. 62/469,646, filed Mar. 10, 2017, the disclosure of which is hereby incorporated by reference herein.

BACKGROUND OF THE DISCLOSURE

The present disclosure relates to heart valve replacement and, in particular, to the delivery of collapsible prosthetic heart valves into a patient for implantation. More particularly, the present disclosure relates to devices and methods for transseptal delivery of a collapsible prosthetic heart valve to a native mitral valve annulus, and to deployment of the prosthetic heart valve at the native mitral valve annulus.

Prosthetic heart valves that are collapsible to a relatively small circumferential size can be delivered into a patient less invasively than valves that are not collapsible. For example, a collapsible valve may be delivered into a patient via a tube-like delivery apparatus such as a catheter, a trocar, a laparascopic instrument, or the like. This collapsibility can avoid the need for a more invasive procedure such as full open-chest, open-heart surgery.

Collapsible prosthetic heart valves typically take the form of a valve structure mounted on a stent. There are two types of stents on which the valve structures are ordinarily mounted: a self-expanding stent and a balloon-expandable stent. To place such valves into a delivery apparatus and ultimately into a patient, the valve is generally first collapsed or crimped to reduce its circumferential size.

When a collapsed prosthetic valve has reached the desired implant site in the patient (e.g., at or near the annulus of the patient's heart valve that is to be replaced by the prosthetic valve), the prosthetic valve can be deployed or released from the delivery apparatus and re-expanded to full operating size. For balloon-expandable valves, this generally involves releasing the entire valve, assuring its proper location, and then expanding a balloon positioned within the valve stent. For self-expanding valves, on the other hand, the stent automatically expands as the sheath covering the valve is withdrawn.

Many transcatheter mitral valve replacement devices are delivered by a transapical route, which generally includes passing the delivery device through incisions made in the chest of the patient and in the apex of the heart. However, because they require the chest to be opened and the ventricle wall to be punctured, transapical delivery routes may result in increased trauma compared to percutaneous delivery routes.

BRIEF SUMMARY

According to a first aspect of the disclosure, a delivery device for a collapsible prosthetic heart valve includes a handle and a catheter assembly. The handle may have a first handle portion, a second handle portion and a third handle portion coupled to one another in series. The catheter assembly may be coupled to the handle and include multiple sheaths. A first sheath of the catheter assembly may be coupled to a first handle portion, the first sheath being rotatable about a longitudinal axis of the first sheath, a distal end of the first sheath being bendable relative to a center portion of the first sheath. A second sheath of the catheter assembly may be coupled to the second handle portion and extend through an interior of the first sheath, the second sheath being rotatable about a longitudinal axis of the second sheath and relative to the first sheath and being translatable relative to the first sheath, a distal end of the second sheath being bendable relative to a center portion of the second sheath. A third sheath of the catheter assembly may be coupled to the third handle portion and extend through an interior of the second sheath and the interior of the first sheath, the third sheath being translatable relative to the second sheath. A compartment of the catheter assembly for receiving the prosthetic heart valve in a collapsed condition may be operably coupled to the third sheath.

According to a second aspect of the disclosure, a method of replacing a native mitral valve of a patient includes advancing a delivery device to a right atrium of the patient, the delivery device having a first sheath, a second sheath translatable relative to the first sheath, a compartment having a closed condition and an open condition and being translatable relative to the first sheath and the second sheath, and a collapsible prosthetic heart valve stored in a collapsed condition within the compartment in the closed condition. The first sheath may be advanced toward an opening in a septum wall dividing a left atrium of the patient from the right atrium of the patient. The compartment may be passed through the opening in the septum wall. The second sheath may be translated relative to the first sheath toward the native mitral valve. A distal end of the second sheath may be bent to align the distal end of the second sheath with an annulus of the native mitral valve. The compartment may be translated relative to the second sheath toward the native mitral valve. The compartment may be placed in the open condition and the prosthetic heart valve may be deployed into the annulus of the native mitral valve so that the prosthetic heart valve transitions to an expanded condition.

BRIEF DESCRIPTION OF THE DRAWINGS

Various embodiments of the present invention will now be described with reference to the appended drawings. It is to be appreciated that these drawings depict only some embodiments of the invention and are therefore not to be considered limiting of its scope.

DETAILED DESCRIPTION

As used herein, the term "inflow end," when used in connection with a prosthetic mitral heart valve, refers to the end of the heart valve closest to the left atrium when the heart valve is implanted in a patient, whereas the term "outflow end," when used in connection with a prosthetic mitral heart valve, refers to the end of the heart valve closest to the left ventricle when the heart valve is implanted in a patient. Further, when used herein with reference to a delivery device, the terms "proximal" and "distal" are to be taken as relative to a user operating the device in an intended manner. "Proximal" is to be understood as relatively close to the user and "distal" is to be understood as relatively farther away from the user. Also, as used herein, the terms "substantially," "generally," and "about" are intended to mean that slight deviations from absolute are included within the scope of the term so modified.

Figure 1:
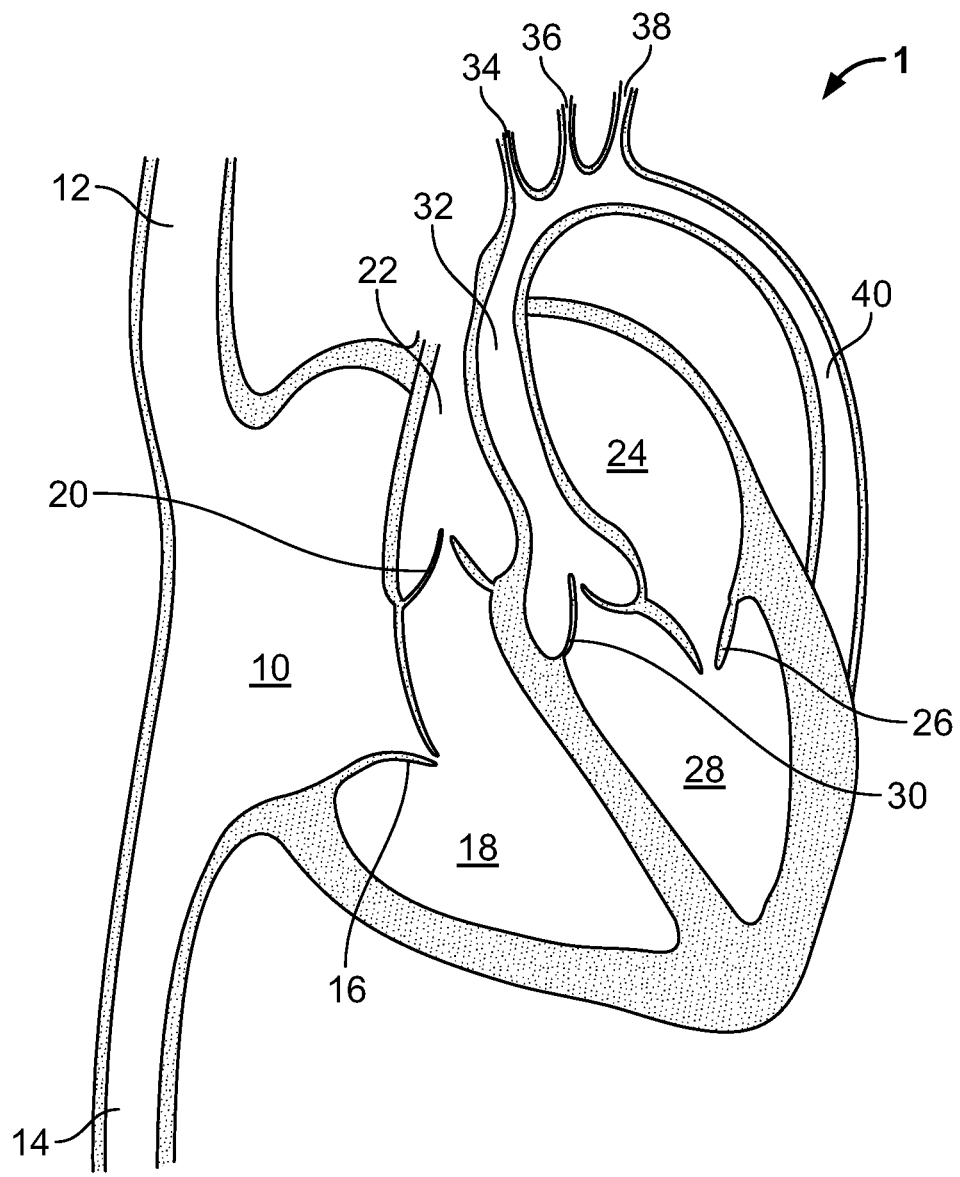
FIG. 1 is a schematic representation of a human heart and associated blood vessels.

FIG. 1 is a schematic view of the human heart 1 and selected blood vessels leading to or from the heart. Briefly, deoxygenated blood enters the right atrium 10 from the superior vena cava 12 and the inferior vena cava 14. The right atrium 10 contracts to force blood through the tricuspid valve 16 and into the right ventricle 18. The right ventricle 18 then contracts to force blood through the pulmonary valve 20 into the pulmonary artery 22 which transports the blood to the lungs to become oxygenated. Oxygenated blood then returns from the pulmonary veins (not illustrated) and flows into the left atrium 24. The left atrium 24 contracts and forces blood through the mitral valve 26 and into the left ventricle 28. The left ventricle 28 contracts to force blood through the aortic valve 30 and into the ascending aorta 32. Blood is transported from the ascending aorta 32 to the rest of the body through a variety of other vessels such as the brachiocephalic artery 34, the left common carotid artery 36, the left subclavian artery 38, and the descending aorta 40.

If the native mitral valve 26 is working improperly, blood may pass from the left ventricle 28 back into the left atrium 24, which may result in inefficient transport of oxygenated blood to the body. This situation may necessitate that the native mitral valve be repaired, if possible, or replaced. There are limited delivery routes to allow the native mitral valve 26 to be replaced with a collapsible prosthetic valve. For example, the apex of the heart wall near the left ventricle 28 may be punctured and a rigid tube may be passed through the left ventricle 28 and into or adjacent the annulus of the native mitral valve 26, with the prosthetic valve then being released and expanded into the native annulus to provide proper valve function between the left atrium 24 and left ventricle 28. However, as noted above, transapical procedures may cause a large amount of trauma compared to other methods that utilize entry to the heart via blood vessels leading to or away from the heart. The pulmonary veins which lead to the left atrium 24, however, may be undesirable for use in delivering of a collapsed prosthetic heart valve. Although prosthetic aortic valves are often delivered to the native aortic valve 30 via the femoral artery and then the aorta, it would be difficult for a catheter that enters the left ventricle 28 via the ascending aorta 32 to be turned sharply to position a prosthetic valve in the annulus of the native mitral valve 26 due to geometrical and special constraints. One solution to reduce trauma relative to a transapical approach is to access the right atrium 10 via the inferior vena cava 14, and then to create a puncture in the septum wall that divides the right atrium 10 from the left atrium 24. The delivery device may then be passed from the right atrium 10 to the left atrium 24 to access the annulus of the native mitral valve 26 so that a prosthetic heart valve may be deployed to take over the functioning of the native mitral valve 26. Although this approach is generally considered less traumatic than a transapical approach, the transseptal delivery route provides a separate set of obstacles. For example, once the delivery device enters the left atrium 24 through the pierced septum, the device preferably is able to turn to align with the center of the annulus of the native mitral valve 26, rotate about a central axis (for orientation dependent valves), and advance so that the device is positioned at or near the center of the annulus. If the delivery device is not positioned at or near the center of the annulus of the native mitral valve 26 upon deployment of the prosthetic heart valve, it may be difficult or impossible to properly seat the prosthetic valve. The rotational position of the prosthetic heart valve may also be important, particularly if the prosthetic valve is shaped to fit the D-shaped native mitral valve annulus, includes asymmetric anchors or other members intended to grasp or otherwise interact with specific areas of the leaflets or annulus of the native mitral valve 26.

Before describing the transseptal delivery device of the present disclosure, examples of prosthetic mitral valves are described.

Figure 2A:
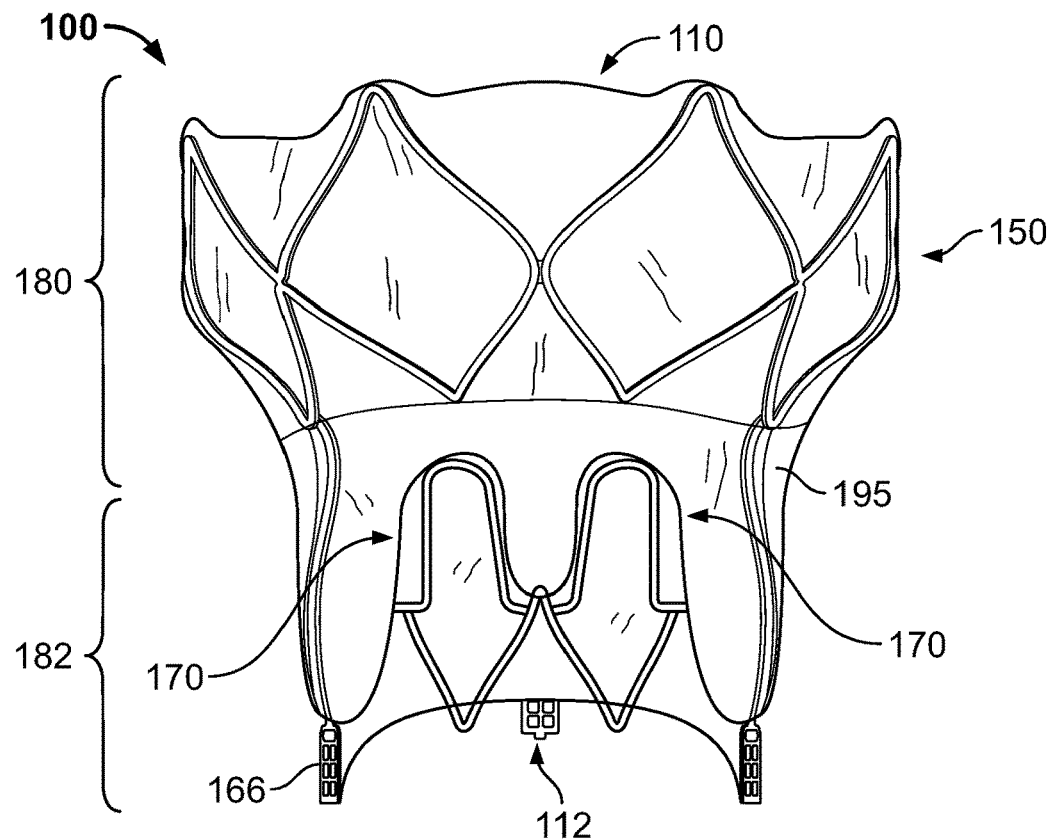
FIG. 2A is a side view of a prosthetic mitral heart valve.
Figure 2B:
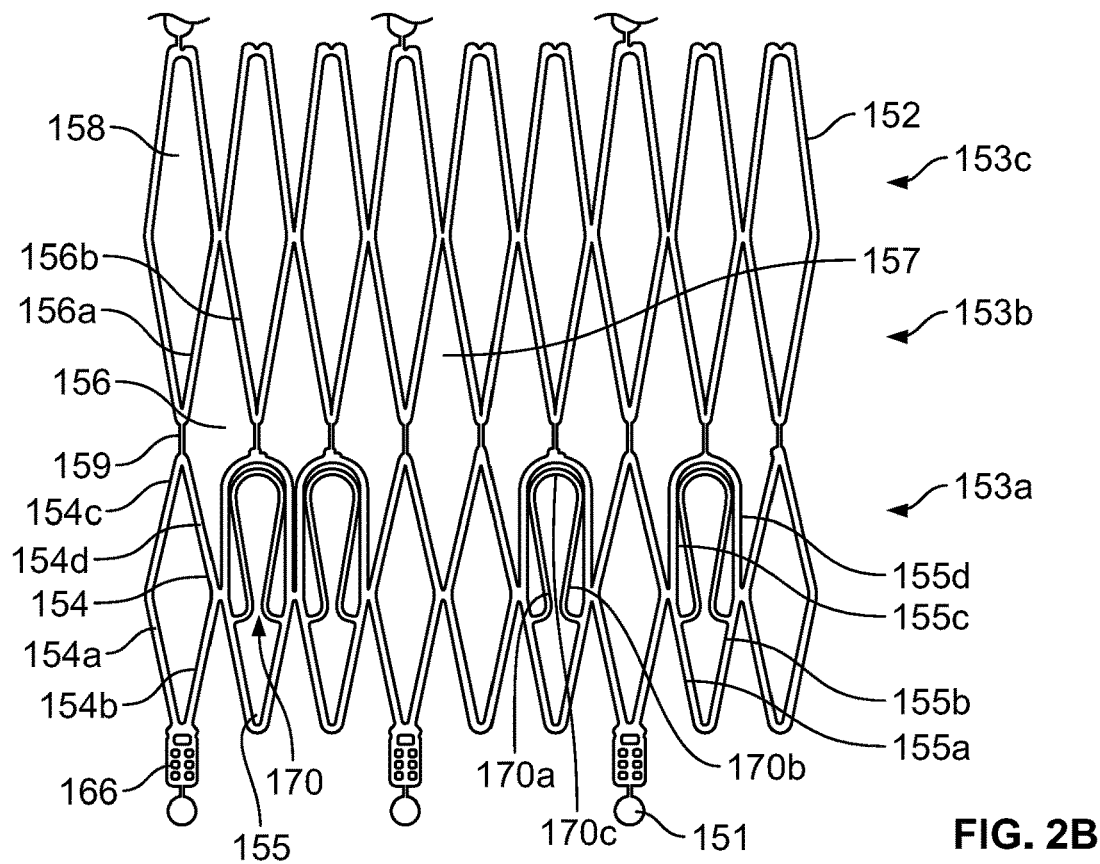
FIG. 2B is a developed view of a stent used in the prosthetic heart valve of FIG. 2A.
Figure 2C:
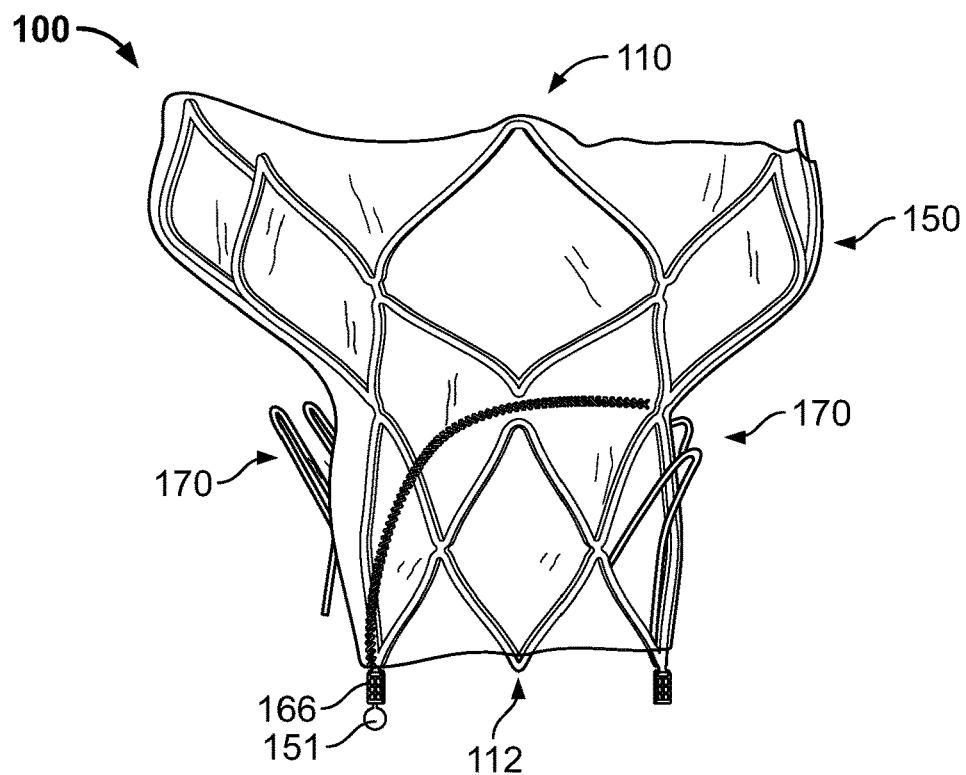
FIG. 2C is a side view of the prosthetic heart valve of FIG. 2A rotated about its longitudinal axis.
Figure 2D:
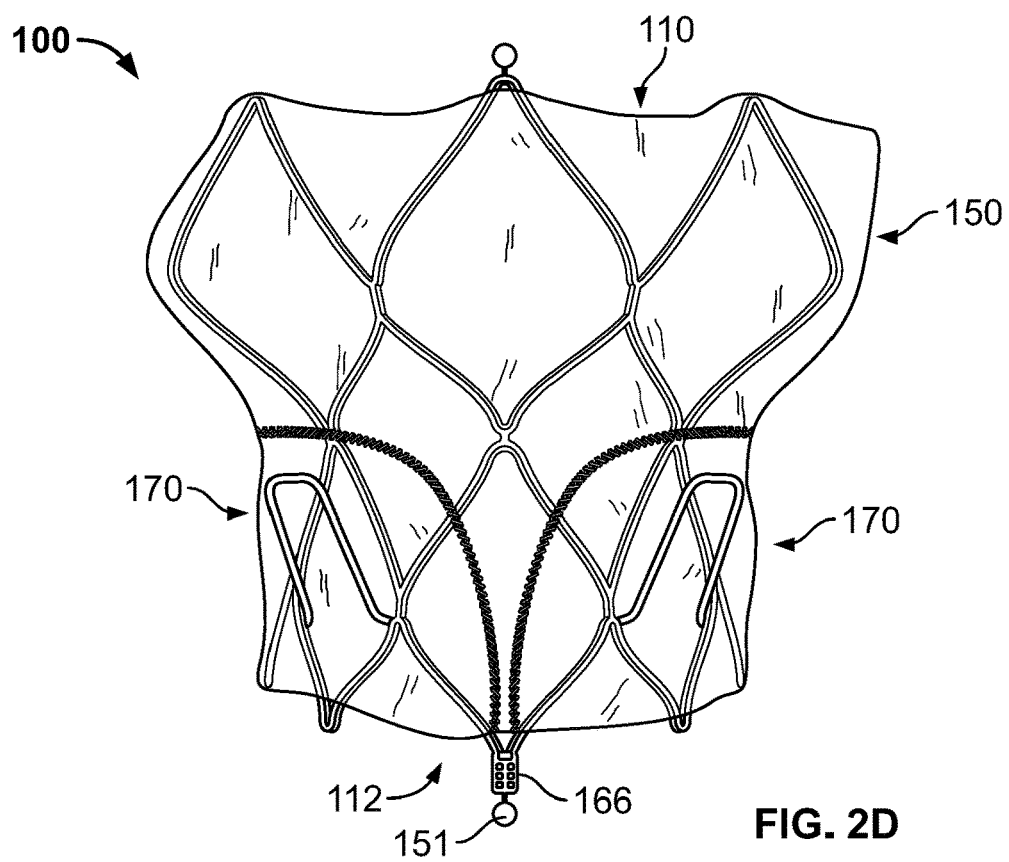
FIG. 2D is a side view of the prosthetic heart valve of FIG. 2A rotated further about its longitudinal axis.

FIG. 2A is side view of prosthetic heart valve 100. Prosthetic heart valve 100 is collapsible and expandable and designed for replacement of a native mitral valve. Prosthetic heart valve 100 has an inflow end 110 and an outflow end 112, and in the expanded condition has a substantially cylindrical portion adjacent outflow end 112, and a flared portion closer to inflow end 110. Prosthetic heart valve 100 includes stent 150, which includes securement features to anchor the prosthetic valve 100 to the anatomy. In particular, and as best shown in FIG. 2B, stent 150 includes a plurality of struts 152 forming three circumferential rows of cells 153*a*, 153*b*, and 153*c*. Commissure attachment features ("CAFs") 166 may be included near the outflow end 112 of stent 150. As shown in FIGS. 2B-D, CAFs 166 may also include retainers 151 extending therefrom for use with a delivery device, such as the devices described herein, although the retainers do not necessarily need to be coupled to the CAFs and may positioned elsewhere on stent 150, including on the inflow end 110 of stent 150.

The first row of cells 153*a* is disposed adjacent outflow end 112 and includes fully symmetric cells 154 and partially symmetric cells 155 at selected positions within the row. Fully symmetric cells 154 may be substantially diamond-shaped and include four substantially straight struts 154*a-d* of equal length. Cells 154 are fully symmetric in that they are symmetric about a vertical line extending from the intersection of struts 154*a* and 154*b* to the intersection of struts 154*c* and 154*d*, and about a horizontal line extending from the intersection of struts 154*a* and 154*c* to the intersection of struts 154*b* and 154*d*. Cells 155 may include a pair of substantially straight struts 155*a*, 155*b* which form a V-shape attached to two substantially curved struts 155*c*, 155*d*. Cells 155 are partially symmetric in that they are symmetric only about a vertical line extending from the intersection of struts 155*a* and 155*b* to the intersection of struts 155*c* and 155*d*. Engaging arms 170 may be nested within each cell 155. Engaging arms 170 are pivotably connected to cells 155 and may be configured to engage portions of heart tissue (e.g., native mitral valve leaflets) when prosthetic heart valve 100 is deployed in a patient. Second row of cells 153*b* may include a plurality of asymmetric cells 156 formed by two struts shared with cells from first row 153*a* (e.g., struts 154*c* and 155*d* or struts 154*d* and 155*c*) and two substantially straight struts 156*a*, 156*b*. Cells 156 may also include runners 159, which connect cells 158 in third row 153*c* to adjacent cells 154 or 155 in first row 153*a*. Second row of cells 153*b* may also include one or more fully symmetric cells 157 substantially similar to fully symmetric cells 154, although the dimensions of fully symmetric cells 157 may be different than those of fully symmetric cells 154. Further, fully symmetric cells 157 may also include runners 159 when they are included in the other cells in second row 153*b*. Third row of cells 153*c* is positioned adjacent inflow end 110 and may include a plurality of enlarged substantially diamond-shaped cells 158 that provide an outwardly flared shape when prosthetic heart valve 100 is in the expanded condition, as described in greater detail below. It should also be noted that the ends of cells 158 nearest inflow end 110 may be blunted or otherwise rounded, rather than V-shaped.

As shown in FIGS. 2A-D, the three rows of cells forming stent 150 each have nine cells. However, it should be understood that prosthetic heart valve 100 may alternatively take a configuration with a different odd number of cells, or an even number of cells, such as a twelve-cell configuration. As shown, first row of cells 153*a* may include two partially symmetric cells 155 adjacent to one another, each having an engaging arm 170 nested therein. First row of cells 153*a* may also include, substantially diametrically opposed to adjacent cells 155, two additional partially symmetric cells 155 separated by a single fully symmetric cell 154, each of the two additional partially symmetric cells 155 having an engaging arm 170 nested therein. This asymmetric configuration of the pairs of engaging arms 170 may help the engaging arms properly engage the leaflets of the native mitral valve, although the pairs of engaging arms may alternatively be positioned in a symmetric fashion, particularly in embodiments in which an even number of cells are included in first row 153*a*. In the illustrated embodiment, second row of cells 153*b* includes cells with four straight struts, cells with three straight struts and a curved strut, and cells with two straight struts and two curved struts.

Each engaging arm 170 may be formed of a shape-memory alloy, and is preferably formed from the same material as stent 150. Engaging arms 170 may include two substantially parallel struts 170*a*, 170*b* connected to one another by rounded strut 170*c*. Engaging arms 170 may be shape set so that the free end of each engaging arm 170 defined by rounded strut 170*c* is positioned radially outwardly from the partially symmetric cell 155 in which the engaging arm is nested. However, forces may be applied to engaging arms 170 and to prosthetic heart valve 100 generally to reduce the radial size and/or bulk of the prosthetic heart valve when in the collapsed condition, which may facilitate intravascular (or other minimally invasive) delivery of the prosthetic heart valve via a delivery device.

In the expanded condition of prosthetic heart valve 100, the cells in the third row 153*c* and portions of the cells in the second row 153*b* flare radially outwardly to form a flared section 180. At the same time, the cells in the first row 153*a* and other portions of the cells in the second row 153*b* form a substantially cylindrical section 182. With this expanded configuration, the diameter of inflow end 110 of stent 150 is greater than the diameter of outflow end 112. Flared section 180 may function to help anchor prosthetic heart valve 100 in the native mitral valve annulus and to prevent paravalvular leak.

Figure 2E:
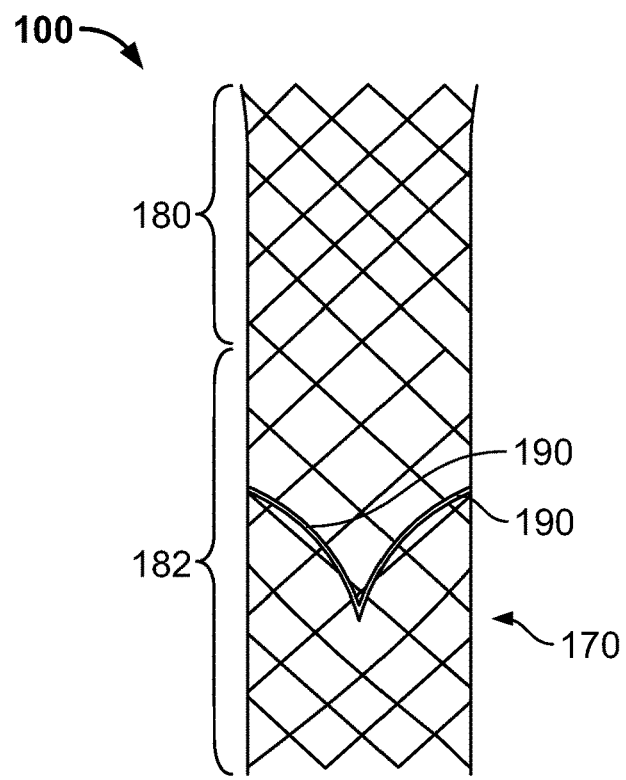
FIG. 2E is a highly schematic longitudinal cross-section of the prosthetic heart valve of FIG. 2A in a collapsed condition.
Figure 2F:
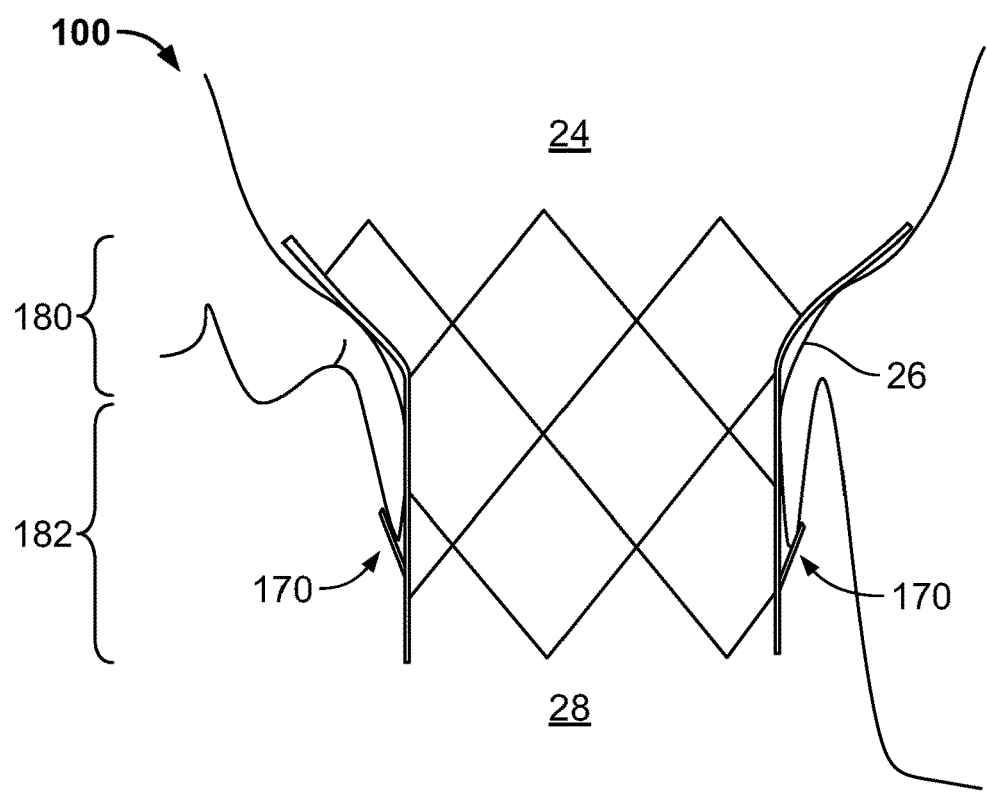
FIG. 2F is a highly schematic representation of the prosthetic heart valve of FIG. 2A implanted into a native mitral valve annulus.

As shown in FIG. 2E, prosthetic heart valve 100 may be transitioned to the collapsed condition, with engaging arms 170 constrained so that each engaging arm 170 is positioned substantially within a surface defined by the partially symmetric cell 155 in which the engaging arm is nested. Flared section 180 may also collapse to a substantially cylindrical profile. Prosthetic heart valve 100 may be held in the collapsed condition by the delivery device as it is delivered to native mitral valve 26, as described in greater detail below. When positioned as desired relative to native mitral valve 26, prosthetic heart valve 100 may be released from the delivery device. As constraining forces are removed from prosthetic heart valve 100, it begins to transition to the expanded condition, while engaging arms 170 and flared section 180 revert to their preset shapes projecting radially outwardly from the rest of stent 150. Once engaging arms 170 are in their preset shape, prosthetic heart valve 100 may be pulled (or pushed) toward left atrium 24 until engaging arms 170 hook under the leaflets of the native mitral valve 26, as shown in FIG. 2F. It is preferable that the pair of engaging arms 170 nested within immediately adjacent partially symmetric cells 155 be hooked under the posterior leaflet of native mitral valve 26, with the pair of engaging arms 170 separated by a fully symmetric cell 154 being hooked under the anterior leaflet of the native mitral valve. As flared section 180 transitions from the collapsed condition to the expanded condition, it begins to expand radially outwardly to the shape illustrated in FIG. 2A. When implanted and in the expanded condition, flared section 180 provides a large surface area to help anchor prosthetic valve 100 within the annulus of native mitral valve 26, and may be particularly effective at resisting movement of prosthetic heart valve 100 toward left ventricle 28. Specifically, flared section 180 has an expanded diameter that is too large to pass through the annulus of the native mitral valve 26. It will therefore be apparent that the combination of engaging arms 170 and flared section 180 helps to securely anchor prosthetic heart valve 100 within the annulus of the native mitral valve 26 and limit its migration toward either the left ventricle 28 or the left atrium 24.

Prosthetic heart valve 100 may also include a valve assembly, including a plurality of leaflets 190 attached to a cuff 195. The leaflets 190 replace the function of the leaflets of the native mitral valve 26. That is, the leaflets 190 coapt with one another to function as a one-way valve. It will be appreciated that prosthetic heart valve 100 may include two, three, or another number of leaflets, as desired. Preferably, the number of CAFs 166 correspond to the number of leaflets 190, with each juncture between a pair of adjacent leaflets being coupled to stent 150 at a CAF 166. The valve assembly of prosthetic heart valve 100 may be substantially cylindrical, or may taper outwardly from outflow end 112 to inflow end 110. Both cuff 195 and leaflets 190 of the valve assembly may be wholly or partly formed of any suitable biological material, such as bovine or porcine pericardium, or biocompatible polymer, such as PTFE, urethanes and the like.

Figure 3:
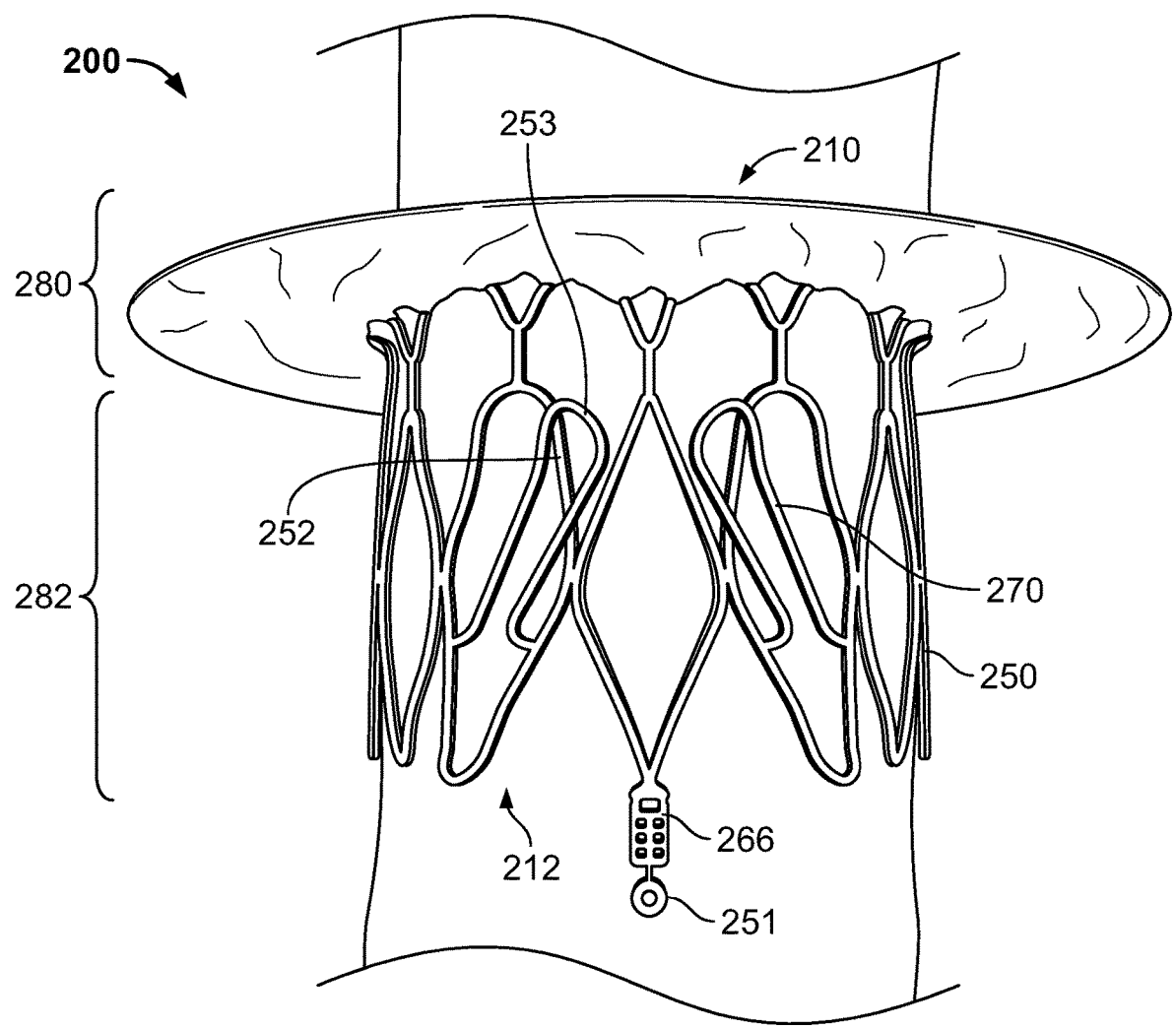
FIG. 3 is a side view of another embodiment of a prosthetic mitral heart valve.

Variations of prosthetic heart valve 100 may also be suitable for implantation into the native mitral valve 26. For example, FIG. 3 illustrates a prosthetic heart valve 200 including a stent 250 extending between an inflow end 210 and an outflow end 212. It should be understood that the valve assembly of prosthetic heart valve 200, including a cuff and leaflets, are omitted from FIG. 3. However, the cuff and leaflets of prosthetic heart valve 200 may be similar or identical to those described above in connection with prosthetic heart valve 100. Stent 250 includes a plurality of struts forming one or more circumferential rows of cells. CAFs 266 similar to CAFs 166 may be included near the outflow end 212 of stent 250. Each CAF 266 may include a retainer 251 extending therefrom, although retainers may alternately be positioned on other portions of stent 250 near outflow end 212. In FIG. 3, prosthetic heart valve 200 is in an expanded condition with a cylindrical tube, which forms no part of the disclosure, extending through the interior of the prosthetic heart valve 200 solely for clarity of illustration. Prosthetic heart valve 200 may be substantially symmetrical so that the portion not visible in FIG. 3 is substantially identical to the visible portion, with the exception that prosthetic heart valve includes two additional CAFs not visible in FIG. 3.

Similar to prosthetic heart valve 100, prosthetic heart valve 200 includes a substantially cylindrical portion 282 and a flared portion 280. Unlike prosthetic heart valve 100, the flared portion 280 of prosthetic heart valve 200 is formed of a braided material coupled to the cylindrical portion 282 of stent 250. Flared portion 280 may include a plurality of braided strands or wires arranged in three-dimensional shapes. In one example, the wires form a braided metal fabric that is both resilient and capable of heat treatment substantially to a desired preset shape. One class of materials which meets these qualifications is shape memory alloys, such as, for example, Nitinol. It is also contemplated that the wires may comprise various materials other than Nitinol that have elastic and/or memory properties, such as spring stainless steel, alloys such as Elgiloy®, Hastelloy®, and MP35N®, CoCrNi alloys (e.g., trade name Phynox®), CoCrMo alloys, NiTiCo alloys, or a mixture of metal and polymer fibers. Depending on the individual material selected, the strand diameter, number of strands, and pitch may be altered to achieve desired properties for flared portion 280. In the illustrated embodiment, stent 250 includes two circumferential rows of cells, one of the rows being formed by braided flared portion 280.

Similar to stent 150, stent 250 may include a number of engaging arms 270. Engaging arms 270 may vary from engaging arms 170 in some aspects. For example, engaging arms 270 may each include a bridging strut 252 and a circular eyelet 253 formed by a loop in the bridging strut. Engaging arms 270 may be tilted at an oblique angle to the longitudinal axis of stent 250, for example, so that the engaging arms flare radially outwardly from the longitudinal axis. Engaging arms 270 may also be tilted so that, for a selected pair of engaging arms, free ends of the engaging arms are positioned closer to one another than base portions coupled to stent 250. Flared portion 280 may be attached to stent 250 via a plurality of connectors, the braided material being crimped together at each connector and coupled to a strut of the stent. In the example shown, a single connector is disposed above each cell of stent 250 such that in a nine-cell stent, nine connectors are provided. In other examples, it may be preferable to couple flared portion 280 to stent 250 via sutures or similar structures so that the flared portion has a hinge-type coupling to stent 250, the benefit of which is described in greater detail below. Additional details of a prosthetic heart valve incorporating stent 250 are described in U.S. Provisional Patent Application No. 62/335,294, the contents of which are hereby incorporated by reference herein.

Figure 4:
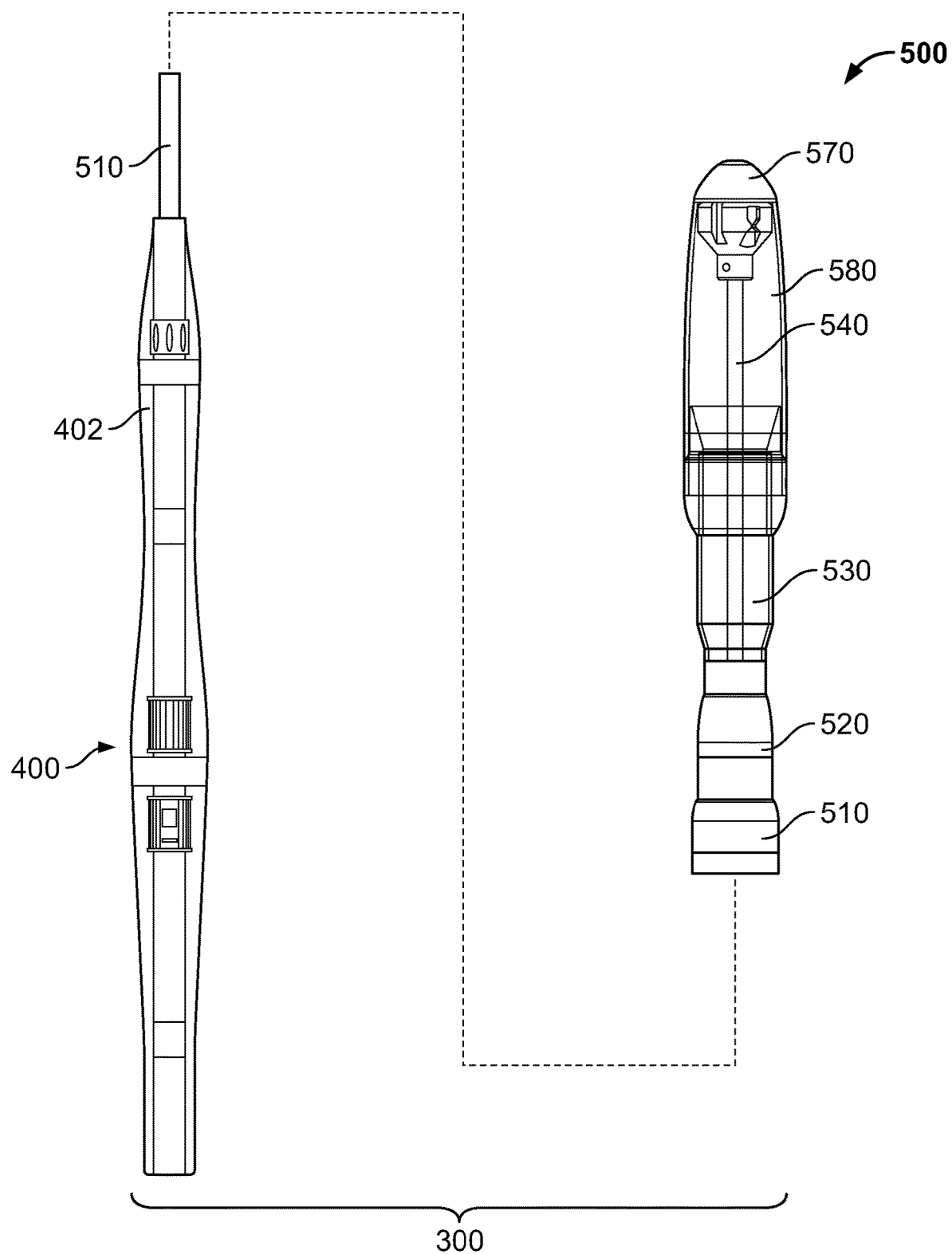
FIG. 4 is a top view of a mitral valve delivery device.

A delivery device 300 for implanting a collapsible prosthetic heart valve, such as prosthetic heart valves 100 and 200, is shown in FIG. 4. Delivery device 300 may include a handle 400 and a catheter assembly 500 extending from the handle. Generally, catheter assembly 500 includes a plurality of catheter sheaths adapted to store the prosthetic heart valve 100 in a collapsed state and to facilitate the introduction of the collapsed prosthetic heart valve to a desired position and in a desired orientation with respect to the native mitral valve 26. As is described in greater detail below, catheter assembly 500 may include a first sheath 510, a second sheath 520, a third sheath 530, a fourth sheath 540, and a fifth sheath 550 (fifth sheath not visible in FIG. 4), although more or fewer sheaths may be used in some embodiments. Catheter assembly 500 defines a compartment 560 between sheath 540 and retaining sheath 580 for holding a prosthetic valve in a collapsed condition. The various sheaths may be moved relative to one another through operation of handle 400 to uncover compartment 560 and deploy the prosthetic heart valve. The handle 400 is adapted to interact with the catheter assembly 500 to facilitate the introduction and positioning of prosthetic heart valve 100 at the desired position and orientation, and further to deploy the prosthetic heart valve into the native mitral valve 26. It should be noted that, in FIG. 4, catheter assembly 500 is shown on a larger scale than handle 400.

Figure 6A:
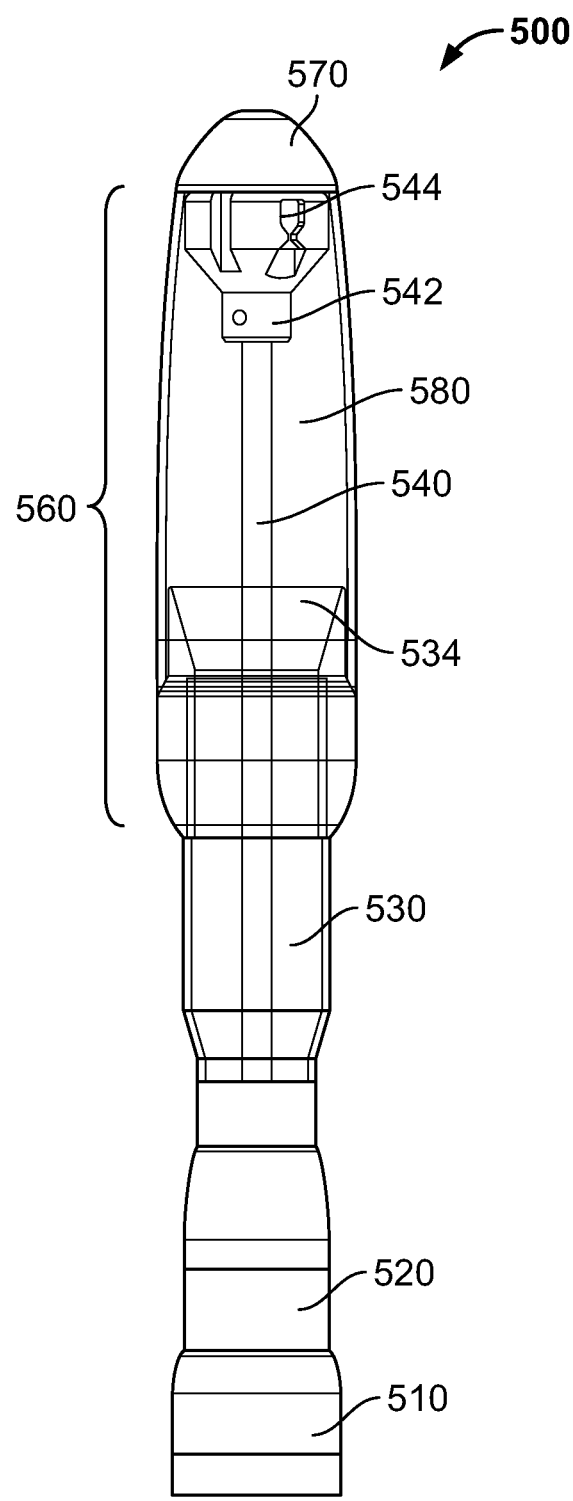
FIG. 6A is a top view of a distal end of a catheter assembly of the delivery device of FIG. 4.
Figure 6B:
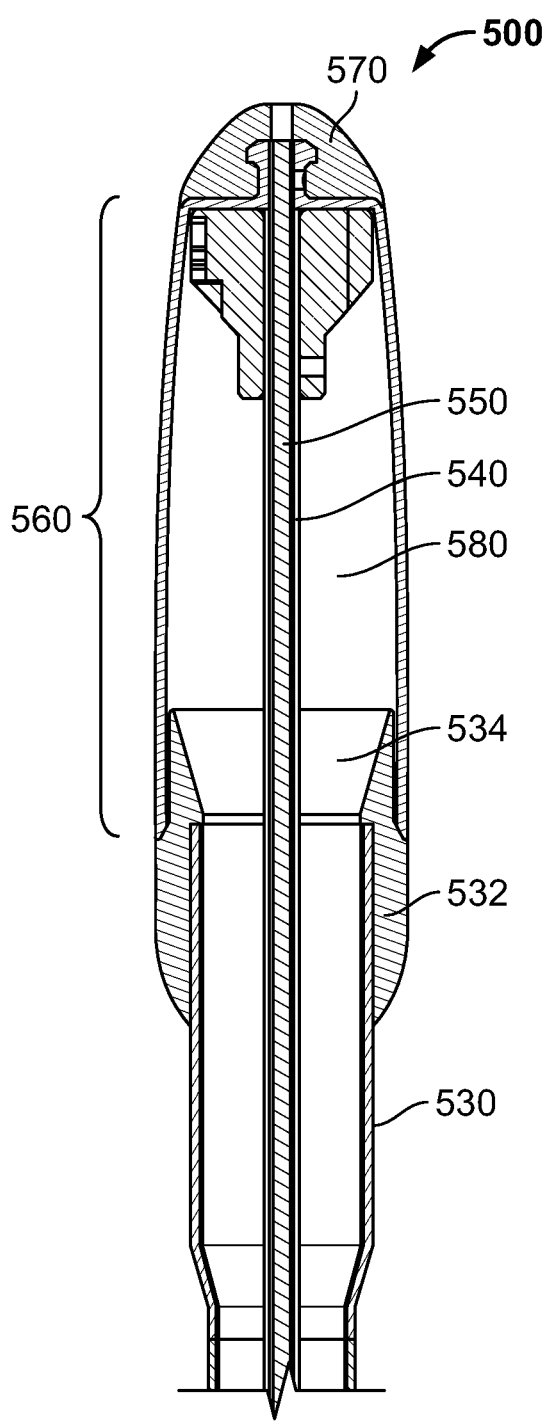
FIG. 6B is a longitudinal cross-section of the distal end of the catheter assembly of FIG. 6A.

An atraumatic tip 570, which is shown in additional detail in FIGS. 6A-B, may be coupled to the distal end of fifth sheath 550. Tip 570 may help facilitate catheter assembly 500 passing through the vasculature while minimizing trauma to the anatomy. Tip 570 is coupled to a retaining sheath 580 that extends from the tip to hub 532 to maintain the prosthetic heart valve in a collapsed state when catheter assembly 500 is in the delivery condition. While retainers 151 of prosthetic heart valve 100 are positioned within retainer recesses 544 and retaining sheath 580 is positioned over the retainer recesses, the prosthetic heart valve remains coupled to compartment 560, thus allowing for resheathing of the prosthetic heart valve prior to its complete deployment.

Figure 5A:
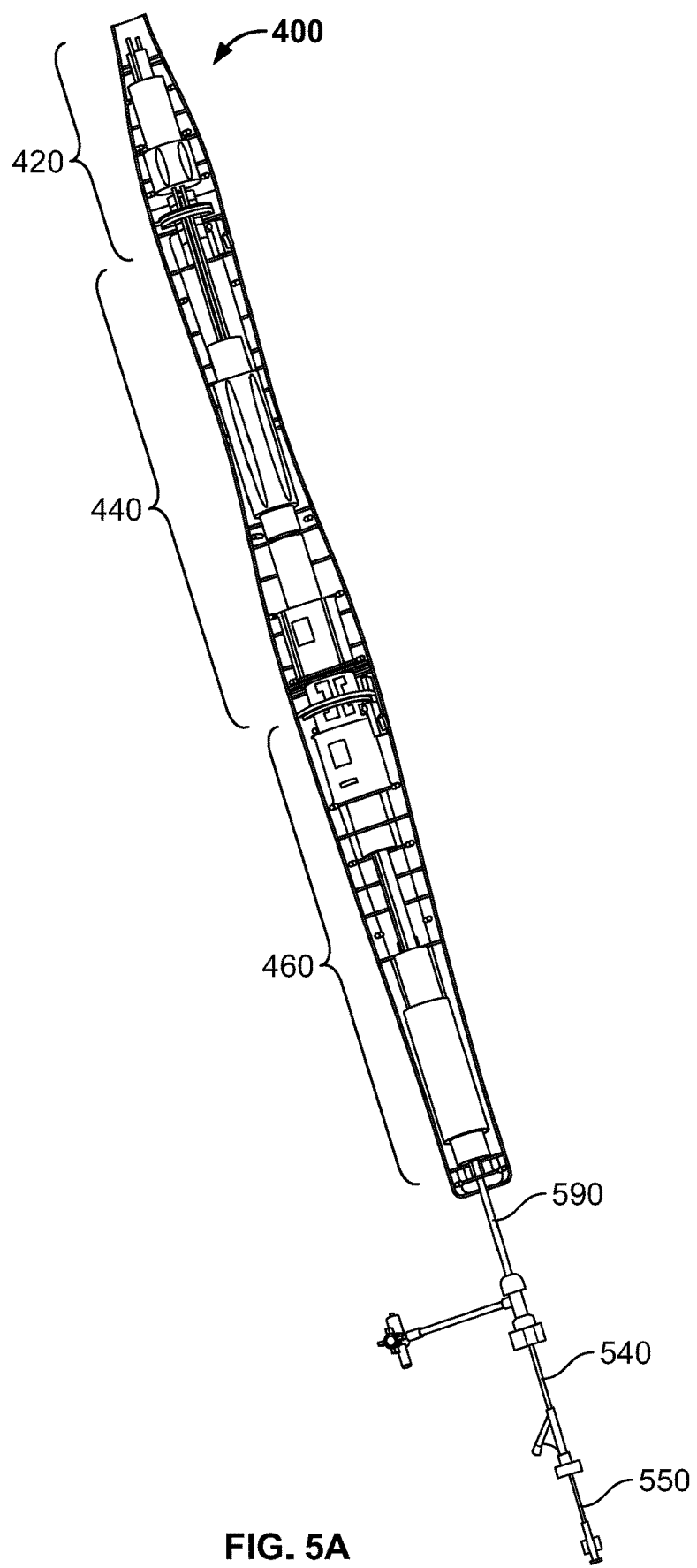
FIG. 5A is a perspective view of a handle of the mitral valve delivery device of FIG. 4.

Handle 400 may include a casing or shell 402 to house various components of delivery device 300. Shell 402 may be formed of a plurality of separate pieces joined together. Handle 400 is illustrated in FIG. 5A with a portion of the shell 402 removed to illustrate internal components of delivery device 300. Handle 400 may include a first handle portion 420, a second handle portion 440, and a third handle portion 460 that together form the complete handle. An additional handle portion (not illustrated) may be provided to assist in controlling fourth sheath 540 and fifth sheath 550.

Figure 5B:
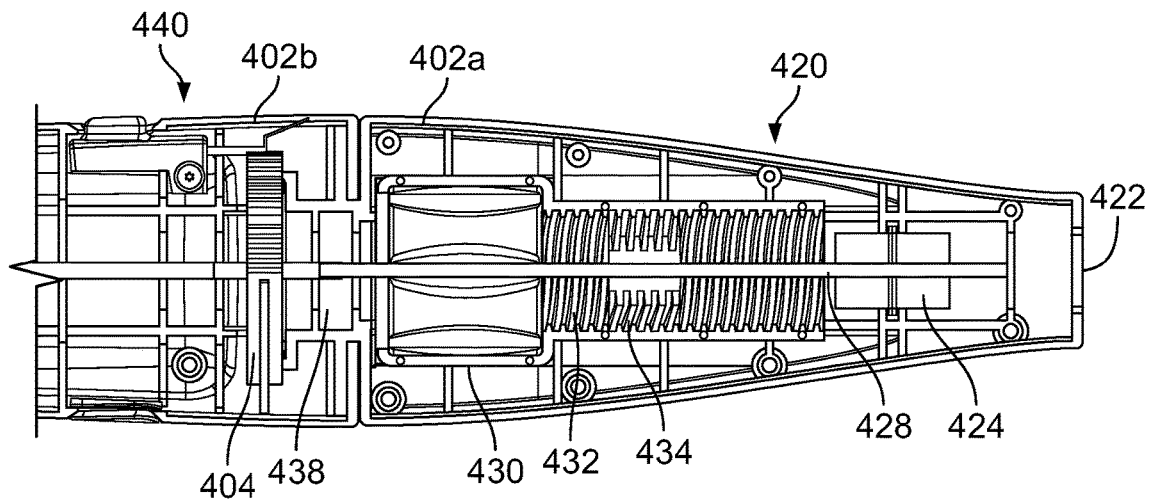
FIGS. 5B-C are side and perspective cut-away views, respectively, of a first portion of the handle of FIG. 5A.
Figure 5C:
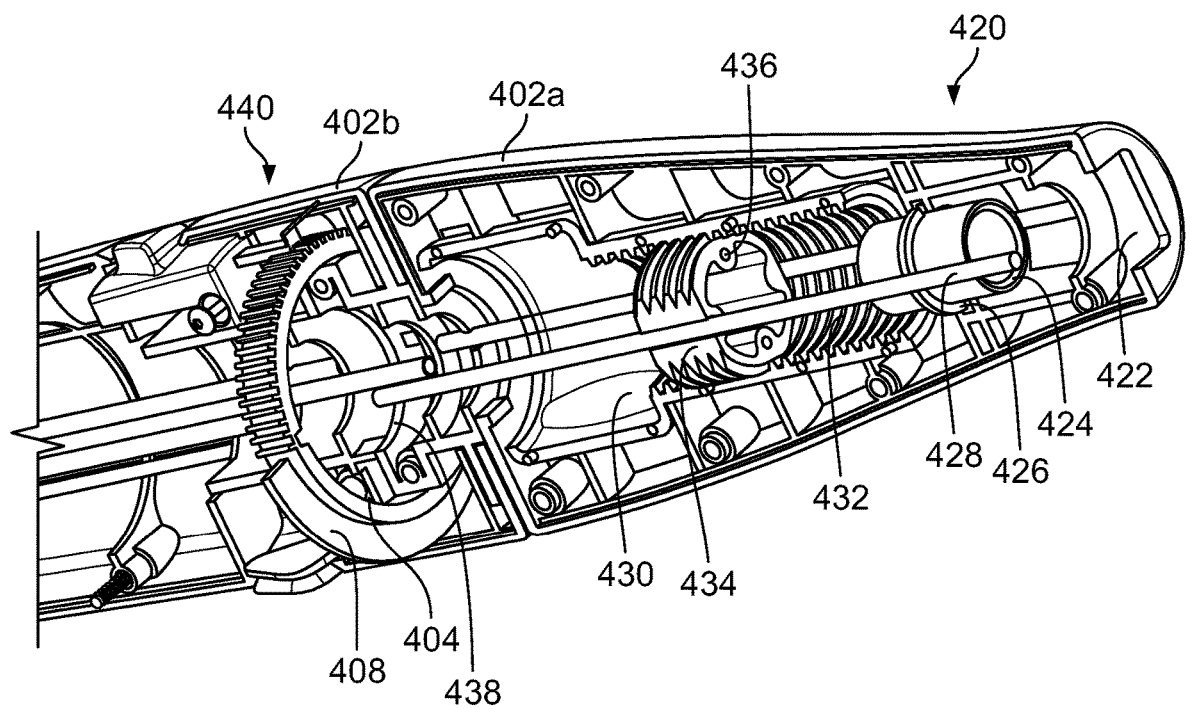

First handle portion 420 is shown in cross-section in FIG. 5B, with a portion of second handle portion 440 to illustrate the interaction between the first and second handle portions. FIG. 5C provides a similar view, with portions of shell 402 omitted, and with certain internal components cut away. In the illustrated embodiment, first handle portion 420 includes a first shell 402a (only half of which is shown) that is coupled to a second shell 402b of second handle portion 440. A distal end of first handle portion 420 may include an opening 422 to allow catheter assembly 500, which is omitted from FIGS. 5A-M, to extend outside handle 400. A first coupling member 424 may be mounted in first shell 402a so that it is rotationally and translationally fixed with respect to the first shell. Coupling member 424 may include a flange 426 or other structure extending into a corresponding groove or slot in first shell 402a to limit the translational movement of the coupling member in the handle. One or more alignment bars 428, described in greater detail below, may engage in one or more notches in the periphery of flange 426 to limit the rotation of coupling member 424 with respect to first shell 402a. A proximal end of first sheath 510 may be bonded or otherwise coupled to a distal portion of coupling member 424 so that sheath 510 is positioned radially inward of at least a portion of the coupling member, although in some embodiments the first sheath may be coupled to the coupling member so that the first sheath is positioned radially outward of a portion of the coupling member. Coupling member 424 may have a hollow interior so that second sheath 520, third sheath 530, fourth sheath 540, and fifth sheath 550 may each pass through the interior of the coupling member and through the interior of first sheath 510.

A first rotation knob 430 may be positioned at least partially within first shell 402a. Half of rotation knob 430 is cut away in FIG. 5C to illustrate internal components. A portion of rotation knob 430 may protrude through a corresponding opening in first shell 402a so that a user may grip and rotate the rotation knob relative to the first shell. First shell 402a may include openings on opposite sides of handle 400 so that rotation knob 430 protrudes from diametrically opposed sides of first handle portion 420. Although rotation knob 430 is rotatable with respect to handle 400, first shell 402a may include internal structures to prevent translation of the rotation knob within the handle. Rotation knob 430 may include an internally threaded tube 432 extending distally within handle 400. An externally threaded drive nut 434 may be positioned within tube 432 and engaged with the threads therein. Preferably, drive nut 434 is hollow so that second sheath 520, third sheath 530, fourth sheath 540, and fifth sheath 550 may all pass through the drive nut. In the illustrated embodiment, drive nut 434 includes two threaded portions on diametrically opposed sides, and two substantially flat portions between the threaded portions. The flat portions of drive nut 434 may each include a groove to receive an alignment bar 428, similar to the notches in the flange 426 of first coupling member 424. The engagement of alignment bars 428 with drive nut 434 prevents rotation of the drive nut relative to handle portion 420, as is described in greater detail below. Through holes 436 may extend from the proximal end to the distal end of drive nut 434, preferably adjacent and radially inward of the two threaded portions. Through holes 436 may each be sized to receive a pull-wire (not illustrated) therethrough. In one embodiment, a single pull-wire may be fixed to drive nut 434 at one of through holes 436 and may extend distally therefrom along a wall of first sheath 510 to a location at or near the distal end of the first sheath. In some embodiments, the pull-wire may terminate in a ring positioned near a distal end of first sheath 510. It should be understood that other pull-wires in other sheaths described herein may similarly terminate in rings in or on the corresponding sheath. The rotation of knob 430 to advance or retract drive nut 434 will push or pull on the pull-wire, causing a distal end of first sheath 510, as well as any additional sheaths positioned within the distal end of the first sheath, to bend relative to a center portion of the first sheath proximal of the distal end, helping to assist in guiding the sheaths through the vasculature. It should be understood that, in some embodiments, retracting a pull wire will cause bending of the corresponding sheath, while advancing the pull wire following retraction will tend to return the sheath back to a non-bent configuration.

As noted above, one or more alignments bars 428 may be positioned within first shell 402a. In the illustrated embodiment, two substantially rigid alignment bars 428 are provided. Preferably, each alignment bar 428 extends from near a distal end of first shell 402a to near a proximal end of the first shell. A groove or slot may be formed at each end of first shell 402a to receive each alignment bar 428, although additional grooves or slots may be provided to impart additional support to the alignment bars. With this configuration, each alignment bar 428 is supported near its ends by first shell 402a. In some embodiments, alignment bars 428 may be fixed via adhesives, friction fits, or other suitable means. However, the interaction of alignment bars 428 with the respective grooves or slots and other structures within first shell 402a may be sufficient to fix the alignment bars 428 without additional fixation means being required. Each alignment bar 428 extends through an interior of rotation knob 430 and through corresponding grooves or notches in drive nut 434 and the flange 426 of coupling member 424, as described above.

A user may manually rotate knob 430 by gripping and rotating one or both portions of the knob exposed through the corresponding openings in first shell 402a. As rotation knob 430 rotates, alignment bars 428 within the grooves in drive nut 434 prevent the drive nut from rotating with it. Since rotation knob 430 is unable to translate within handle 400, rotation of knob 430 causes drive nut 434 to translate with respect to the rotation knob and first shell 402a, the direction of translation depending on the direction in which knob 430 is rotated. Because the pull-wire is fixed at one end to drive nut 434 and at the other end to a distal portion of first sheath 510, rotation of knob 430 results in the bending of first sheath 510. In particular, translation of drive nut 434 proximally causes bending in first sheath 510, while translation of drive nut 434 distally causes the first sheath to tend to return to the unbent condition.

First handle portion 420 may have a first state in which it is rotationally engaged with second handle portion 440, and a second state in which it is rotationally disengaged from the second handle portion. In the rotationally disengaged state, first handle portion 420 is rotatable about its longitudinal axis with respect to second handle portion 440. In the rotationally engaged state, first handle portion 420 is rotationally fixed with respect to second handle portion 440, although both portions may be rotated in unison about an axis extending through the first and second handle portions, as described in greater detail below.

Figure 5D:
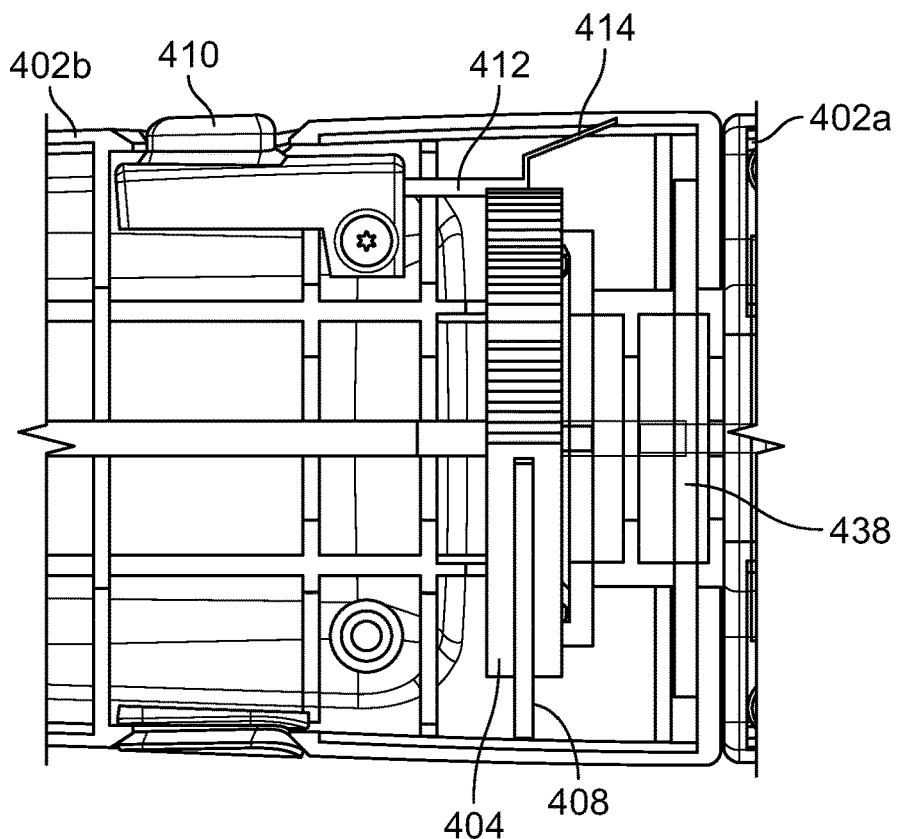
FIGS. 5D-E are enlarged side and perspective cut-away views, respectively, of a rotational engagement mechanism of the handle of FIG. 5A.
Figure 5E:
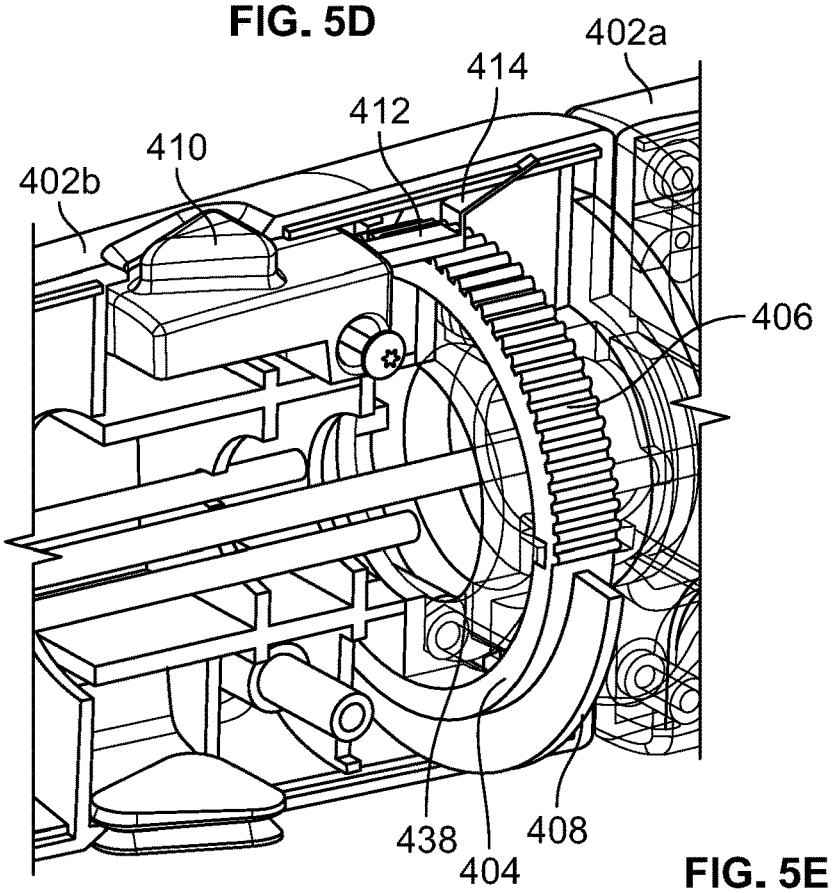

To effect the rotational connection between first handle portion 420 and second handle portion 440, a generally cylindrical connector 438 extends from the proximal end of the first handle portion into the distal end of the second handle portion. Referring to FIGS. 5D-E, connector 438 includes a proximalmost end fixedly engaged to an annular ring 404. As illustrated, ring 404 extends around the circumference of the proximalmost end of connector 438, although in other embodiments the ring may be coupled to other portions of the first shell. Ring 404 may be rotatably fixed to connector 438, for example by ribs of the connector extending into grooves on the inner surface of the ring, or vice versa, or by any other suitable method, including adhesives, etc. At least a portion of the outer circumference of ring 404 may include a plurality of teeth 406. In the illustrated embodiment, teeth 406 extend along approximately half of the circumference of ring 404, although the teeth may extend along a greater or lesser extent of the ring depending on the desired range of rotation of first handle portion 420 relative to second handle portion 440. Although ring 404 is rotatably fixed to connector 438, it may be selectively freed to rotate within second handle portion 440. A rib 408 may project radially from a portion of the circumference of ring 404 to limit the range of rotation of the ring, as described in greater detail below.

The ability of ring 404 to rotate within second handle portion 404 may be controlled by an engagement mechanism that includes a button 410 extending through an outer surface of second shell 402b and a pawl 412 extending from the button toward ring 404. Pawl 412 may be substantially rigid and may include prongs to engage a tooth 406 on the outer circumference of ring 404 such that, when the prongs of the pawl are positioned on each side of the tooth, the ring is unable to rotate, and thus first handle portion 420 is unable to rotate with respect to second handle portion 440. A flat spring 414 may extend at an angle from pawl 412 and contact an inner surface of second shell 402b. In the rotationally engaged state, shown in FIGS. 5D-5E, which may be the default state, spring 414 biases pawl 412 into engagement with the teeth 406 on ring 404. Spring 414 is preferably flexible enough that when a user depresses button 410, the spring flexes and allows the prongs of pawl 412 to lift away from teeth 406 of ring 404 to the rotationally disengaged state. In this state, the prongs of pawl 412 clear teeth 406 so that first handle portion 420 may rotate with respect to second handle portion 440. If a user releases the force applied to button 410, spring 414 will bias pawl 412 back into engagement with teeth 406, reverting to the rotationally engaged state. It will be appreciated that, rather than flat spring 414, any other known biasing member may be employed to bias pawl 412 into engagement with teeth 406.

It should be understood that because first shell 402a is coupled to first sheath 510, as described above, rotation of first handle portion 420 relative to second handle portion 440 results in rotation of the first sheath, but not rotation of any of the other sheaths positioned within the first sheath. Even if a pull-wire in first sheath 510 provides bending in a single direction (e.g. only under tension), such bending in combination with the ability to rotate first sheath 510 allows for significant maneuverability of the first sheath. For example, first sheath 510 may be able to rotate up to about 180 degrees. The directionality of the bending provided by the pull-wire in first sheath 510 may be designed to correspond to the anatomy so that any variations in the anatomy may be accommodated by the ability of the first sheath to rotate. In the illustrated embodiment, first handle portion 420 has a range of rotation of about 180 degrees relative to second handle portion 440. As noted above, this limitation is provided by rib 408. If a user places first handle portion 420 in a rotationally disengaged state with respect to second handle portion 440, the user may rotate the first handle portion in either direction until rib 408 contacts pawl 412. In other words, even in the rotationally disengaged state, rib 408 extends a great enough distance radially away from ring 404 that the ends of the rib can contact pawl 412, limiting further rotation of the ring and, hence, further rotation of first handle portion 420. Although shown as continuous from one end to the other end, it should be understood that rib 408 may take other forms, for example two discrete fingers or stops extending radially outward from ring 404. The degree of available rotation of first handle portion 420 with respect to second handle portion 440 may be altered in other embodiments by increasing or decreasing the arc length of rib 408, or otherwise positioning stops a greater or lesser circumferential distance from one another. In either case, it is preferable that rib 408 (or similar stops) be positioned adjacent the ends of the plurality of teeth 406 so that, regardless of the rotational position of ring 404 with respect to pawl 412, the pawl will always engage a tooth when button 410 is released. The spacing between adjacent teeth 406 may allow first housing portion 420 to be rotationally locked with respect to second housing portion 440 in increments of between about 3 degrees and about 5 degrees, although other spacing that provides other increments of rotation may be suitable.

Figure 5F:
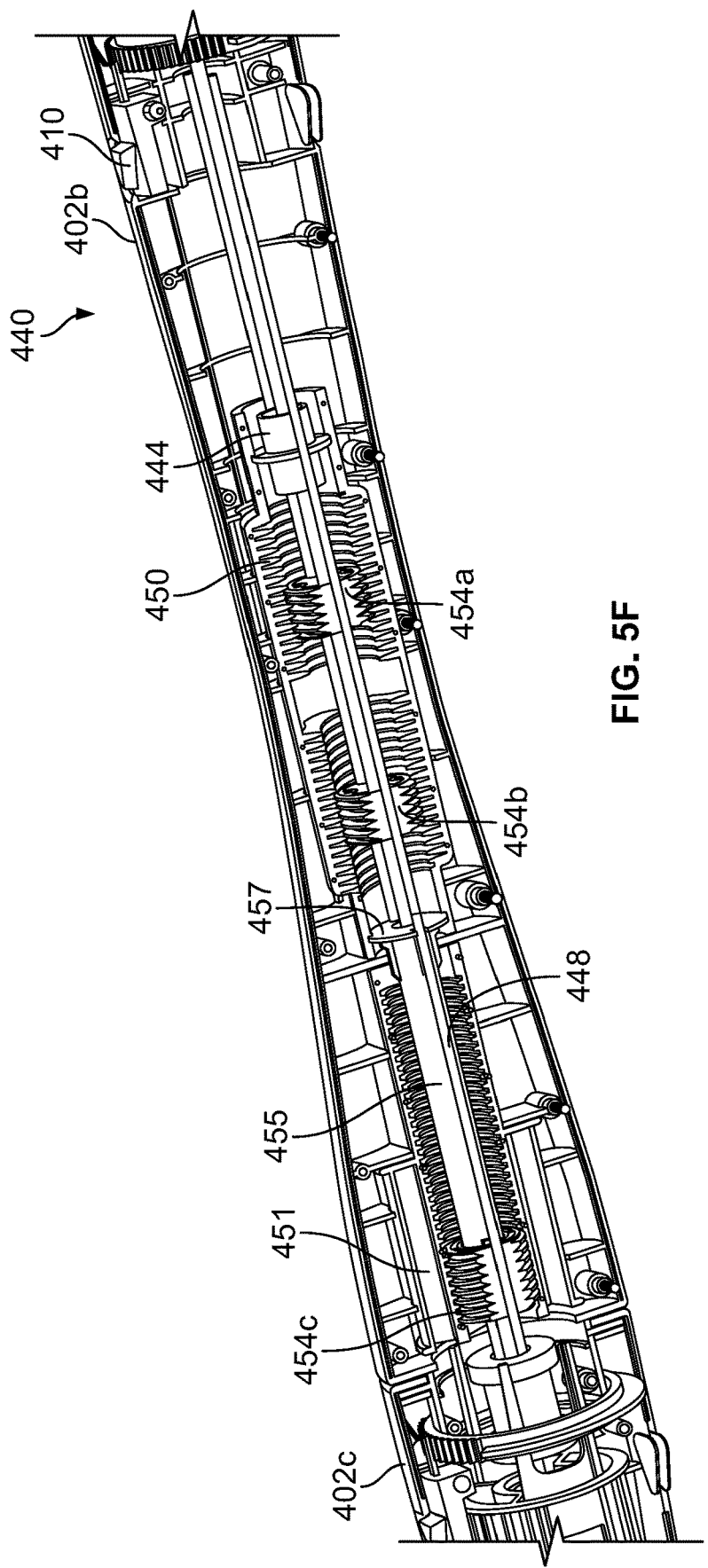
FIG. 5F is a perspective cut-away view of a second portion of the handle of FIG. 5A.
Figure 5G:
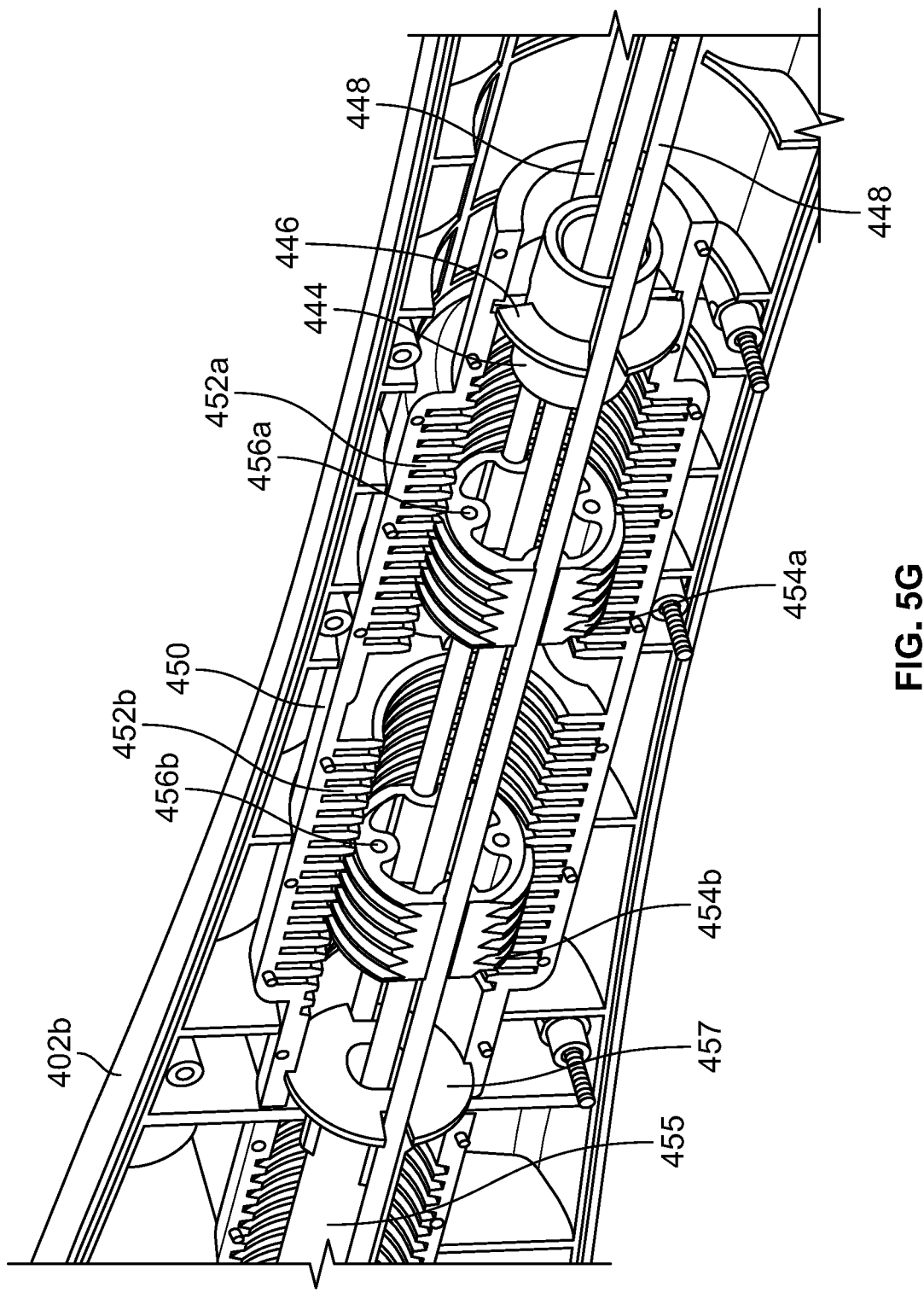
FIG. 5G is an enlarged perspective cut-away view of a rotation knob of the second handle portion of FIG. 5F.
Figure 5H:
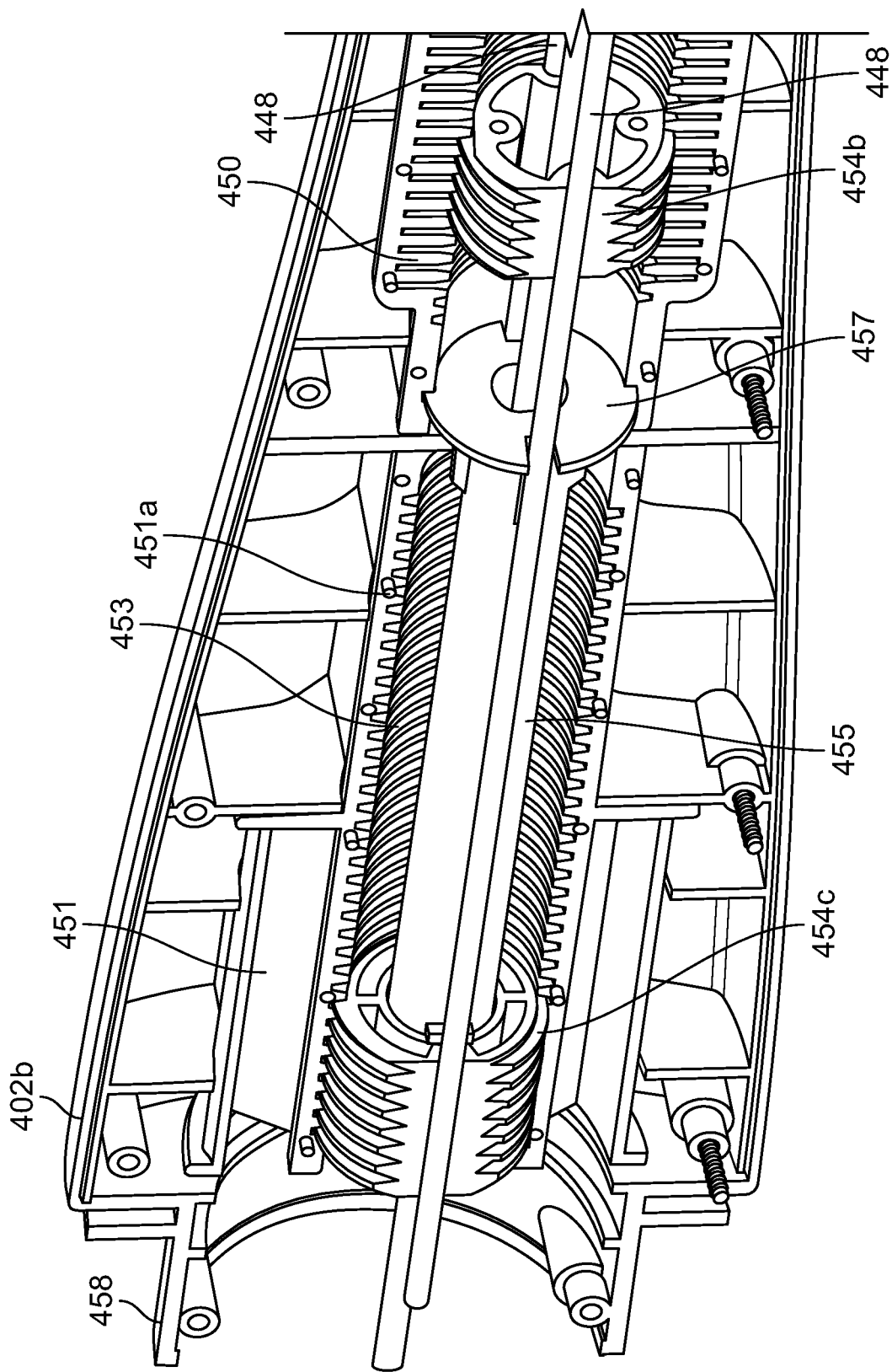
FIG. 5H is an enlarged perspective cut-away view of a linear drive knob of the second handle portion of FIG. 5F.

FIGS. 5F-H illustrate second handle portion 440 with part of second shell 402b omitted to illustrate interior components. A second coupling member 444 may be coupled to second rotation knob 450 so that it is rotationally fixed with respect to second shell 402b and translationally fixed with respect to the second rotation knob. Coupling member 444 may be substantially similar in form and function to first coupling member 424, and may include a flange 446 or other structure extending into a corresponding groove or slot within rotation knob 450 to limit the translational movement of the second coupling member with respect to the second rotation knob. One or more alignment bars 448 may engage in one or more notches formed in the periphery of flange 446 to limit the rotation of coupling member 444 with respect to second shell 402b. A proximal end of second sheath 520 may be bonded or otherwise coupled to a distal portion of coupling member 444 so that the second sheath is positioned within a portion of the coupling member, although in other embodiments the second sheath may be coupled so that it is positioned radially outward of at least a portion of the coupling member. Although first coupling member 424 and second coupling member 444 are similar in structure, second coupling member 444 preferably has a smaller diameter so that second sheath 520 may be coupled to an interior of the second coupling member and also extend distally through an interior of the first coupling member and first sheath 510. Second coupling member 444 may have a hollow interior so that third sheath 530, fourth sheath 540, and fifth sheath 550 may each pass from within second sheath 520 through the interior of the second coupling member.

Rotation knob 450 may be positioned at least partially within second shell 402b. Half of rotation knob 450 is cut away in FIGS. 5F-H to illustrate components interior to the rotation knob. A portion of rotation knob 450 may protrude through a corresponding opening in second shell 402b so that a user may grip and rotate the rotation knob relative to the second shell. Second shell 402b may include openings on opposite sides of handle 400 so that rotation knob 450 protrudes from diametrically opposed sides of second handle portion 440. Unlike first rotation knob 430, second rotation knob 450 may be both rotatable and translatable within handle 400. In that regard, the openings on opposite sides of second shell 402b are shorter than the protruding portions of rotation knob 450 so that the rotation knob is always accessible to the user, regardless of its translational position with respect to the openings. Rotation knob 450 may be hollow, with two internally threaded portions 452a, 452b. An externally threaded drive nut 454a may be threadedly engaged within threaded portion 452a, and another externally threaded drive nut 454b may be threadedly engaged within threaded portion 452b. Preferably, drive nuts 454a and 454b are each hollow so that third sheath 530, fourth sheath 540, and fifth sheath 550 may all pass through these drive nuts. Drive nuts 454a and 454b may be substantially similar to one another and to drive nut 424. In the illustrated embodiment, drive nut 454a and drive nut 454b each include two threaded portions on diametrically opposed sides, and two substantially flat portions between the threaded portions. The flat portions of drive nuts 454a and 454b may each include a groove to receive an alignment bar 448. Similar to drive nut 424, the engagement of alignment bars 448 with drive nuts 454a and 454b prevents rotation of these drive nuts relative to handle portion 440. Through holes 456a may extend from the proximal end to the distal end of drive nut 454a, preferably adjacent and radially inward of the threaded portions. Similar through holes 456b may extend from the proximal end to the distal end of drive nut 454b. Through holes 456a, 456b may each be sized to receive a pull-wire (not illustrated) therethrough. In one embodiment, a first pull-wire may be fixed to drive nut 454a at one of through holes 456a and may extend distally therefrom along a wall of second sheath 520 and to a ring in or on the second sheath. A second pull-wire may be fixed to drive nut 454b at one of through holes 456b and may extend distally therefrom along a wall of second sheath 520, terminating at or near a distal end of the second sheath at a ring. The first and second pull wires preferably extend along diametrically opposite sides of second sheath 520. As explained more fully below, each pull-wire may be advanced or retracted by a respective one of drive nuts 454a and 454b to cause a distal end of the second sheath 520, as well as any additional sheaths positioned within the distal end of the second sheath, to bend relative to a center portion of the second sheath positioned proximal of the distal end, to assist in positioning the sheaths inside the heart.

In the illustrated embodiment, the two alignment bars 448 are substantially rigid. Preferably, each alignment bar 448 extends from near a distal end of second shell 402b to near a proximal end of the second shell. A groove or slot may be formed at each end of second shell 402b to receive each alignment bar 448, although additional grooves or slots may be provided to impart additional support to the alignment bars. With this configuration, each alignment bar 448 is supported near its ends by second shell 402b. However, in some embodiments, certain components such as linkage mechanism 479 (described in greater detail below) may interfere with the ability of proximal ends of alignment bars 448 to couple to groves of second shell 402b. In those embodiments, other structures may be provided to facilitate stabilizing the proximal end of alignment bars 448. Each alignment bar 448 extends through an interior of rotation knob 450 and through corresponding grooves or notches in drive nut 454a, drive nut 454b, and the flange 446 of coupling member 444. Each alignment bar 448 also extends through the interior of a linear drive knob 451 and tubular portion 451a, as well as through corresponding grooves or notches in another drive nut 454c and the flange of a piston 455, all of which will be explained below.

At its proximal end, rotation knob 450 may be coupled to the distal end of a piston 455 so that the knob is able to rotate but not translate relative to the piston. A user may manually rotate knob 450 by gripping and rotating one or both portions of the knob exposed through the corresponding openings in second shell 402b. As rotation knob 450 rotates, the engagement of alignment bars 448 within the grooves in drive nuts 454a and 454b prevent the drive nuts from rotating with it. However, because of its connection to piston 455, described in greater detail below, rotation of knob 450 does not result in translation of the knob within handle 400. As a result, rotation of knob 450 causes drive nut 454a and drive nut 454b to translate simultaneously with respect to the rotation knob and second shell 402b. Preferably, the threads of threaded portion 452a and drive nut 454a are angled in a direction opposite the threads in threaded portion 452b and drive nut 454b (one is right-handed while the other is left-handed) so that rotation of knob 450 causes the drive nuts to translate toward one another or away from one another depending on the direction of rotation of the knob. With this configuration, rotation of knob 450 causes the pull-wire on one side of second sheath 520 to pull while the pull-wire on the opposite side of the second sheath pushes. The use of two drive nuts 454a, 454b may thus provide for bending of second sheath 520 in either direction, as rotation of knob 450 will cause tension on one of the two pull-wires and cause bending in the direction of the tension, with the direction or rotation determining the side the second sheath 520 on which tension is applied.

FIG. 5H illustrates a proximal end of second handle portion 440, with third handle portion 460 omitted and portions of second shell 402b, rotation knob 450, and a linear drive knob 451 cut away to illustrate internal components. Linear drive knob 451 may be positioned in second handle portion 440 proximally of rotation knob 450. A portion of drive knob 451 may protrude through corresponding openings in second shell 402b so that a user may grip and rotate the drive knob relative to the second shell. While drive knob 451 is rotatable relative to handle 400, second shell 402b may include internal structures that prevent the drive knob from translating within the handle. Drive knob 451 may include internal threads 453 along its length, including along the interior of a tubular portion 451a extending distally toward rotation knob 450. An externally threaded drive nut 454c is positioned within drive knob 451 in engagement with threads 453. Drive nut 454c may be substantially similar to drive nuts 434, 454a and 454b.

However, as drive nut 454c need not be configured to couple to pull-wires, it may omit the through holes provided in these other drive nuts. The flat portions of drive nut 454c may each include a groove to receive an alignment bar 448 so that rotation of drive knob 451 translates the drive nut without rotating it. Drive nut 454c and piston 455 both may be hollow so that third sheath 530, fourth sheath 540, and fifth sheath 550 may all pass through the drive nut and piston. Piston 455 may extend through drive knob 451 with its proximal end translationally and rotationally fixed to drive nut 454c. The distal end of piston 455 may project out from the distal end of tubular portion 451a and include a flange 457 that is captured within a corresponding groove near the proximal end of rotation knob 450. The periphery of flange 457 may include notches to receive alignment bars 448 to keep piston 455 rotationally fixed with respect to second shell 402b. The engagement of flange 457 with rotation knob 450 translationally fixes rotation knob 450 with respect to piston 455. As a result, rotation of drive knob 451 causes drive nut 454c to translate within the drive knob and tubular portion 451a, causing a corresponding translation of piston 455 and rotation knob 450. As rotation knob 450 translates, coupling member 444 also translates, causing second sheath 520 to translate with respect to first sheath 510.

Figure 5I:
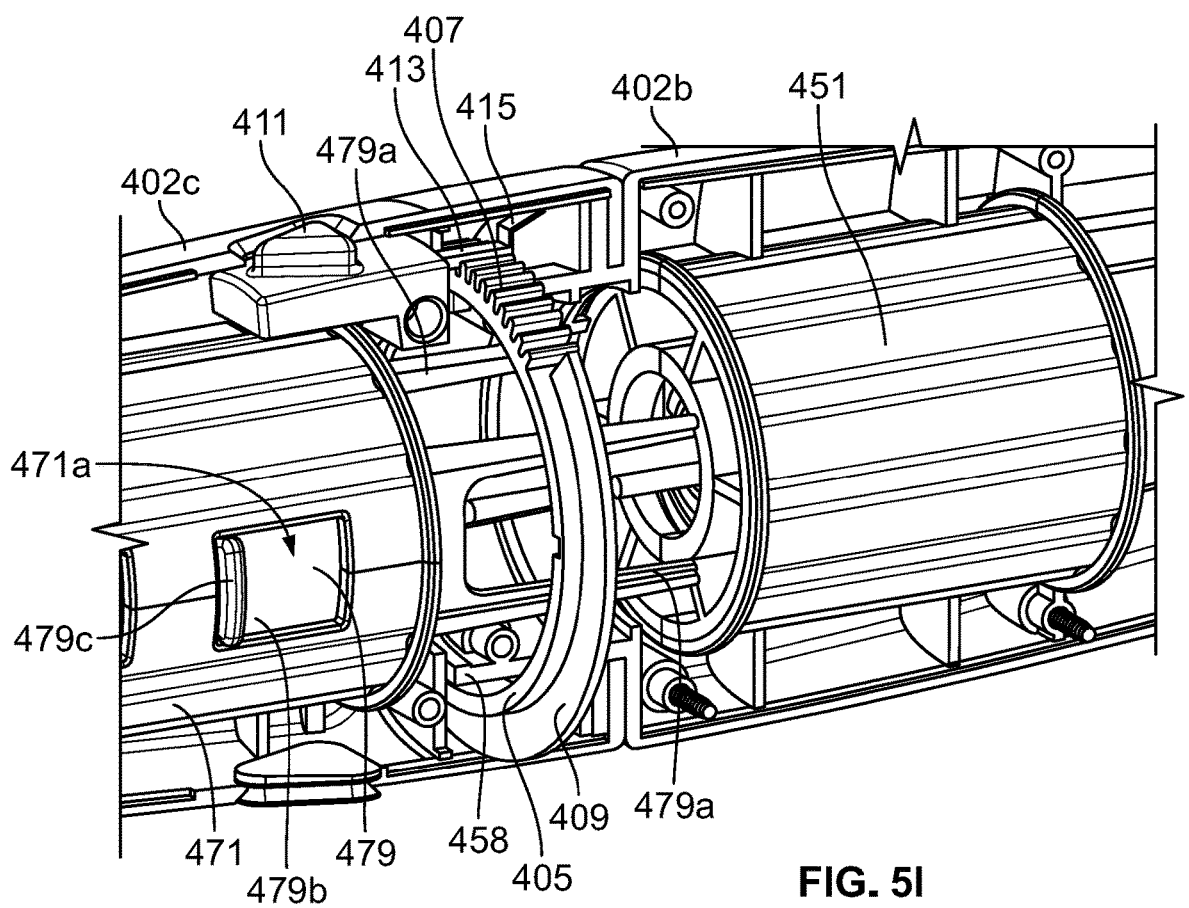
FIG. 5I is an enlarged perspective cut-away view of a translational engagement mechanism of the handle of FIG. 5A.

Referring to FIG. 5I, a generally cylindrical connector 458 extends from the proximal end of second handle portion 440 into the distal end of third handle portion 460. Third handle portion 460 may have a first state in which it is rotationally engaged with second handle portion 440, and a second state in which it is rotationally disengaged from the second handle portion. The structures providing the ability to rotationally engage or disengage third handle portion 460 relative to second handle portion 440 are substantially the same as those described above in connection with the rotational engagement or disengagement of second handle portion 440 relative to first handle portion 420, and are thus described only briefly. Connector 458 may include a proximalmost end to which an annular ring 405 is rotationally fixed. At least a portion of the outer circumference of ring 405 may include a plurality of teeth 407, while another portion of the outer circumference of the ring may include a radially projecting rib 409 to limit the range of rotation of the ring. The ability of ring 405 to rotate within third handle portion 460 may be controlled by an engagement mechanism that includes a button 411 extending through an outer surface of third shell 402c. A pawl 413 extends from button 411 toward ring 405, and a flat spring 415 (or other biasing member) may extend at an angle from the pawl and contact an inner surface of third shell 402c. In the rotationally engaged state, which may be the default state, spring 415 may bias pawl 413 into engagement with the teeth 407 on ring 405. Depressing button 411 disengages pawl 413 from teeth 407 and thereby rotationally disengages third handle portion 460 from second handle portion 440. Ring 405 is not identical to ring 404, however. In particular, teeth 407 extend along a shorter circumferential arc of ring 405 compared to teeth 406 of ring 404. Rib 409, on the other hand, extends a greater circumferential distance around ring 405 compared to rib 408 of ring 404. This configuration results in a lesser total range of rotation of third handle portion 460 relative to second handle portion 440 compared to the total range of rotation of the second handle portion relative to first handle portion 420. However, it should be understood that the length the teeth 407 and rib 409 extend along the circumference of ring 405 may be adjusted to increase or decrease the range of rotation. In the illustrated embodiment, ring 405 may provide for a total range of rotation of about 90 degrees between third handle portion 460 and second handle portion 440. As a result, while handle portion 420 is rotationally engaged to second handle portion 440, and third handle portion 460 is rotationally engaged to the second handle portion, a user may rotate the second handle portion, which in turn rotates the first and third handle portions, resulting in the rotation of first sheath 510, second sheath 520, and third sheath 530 in unison.

Figure 5J:
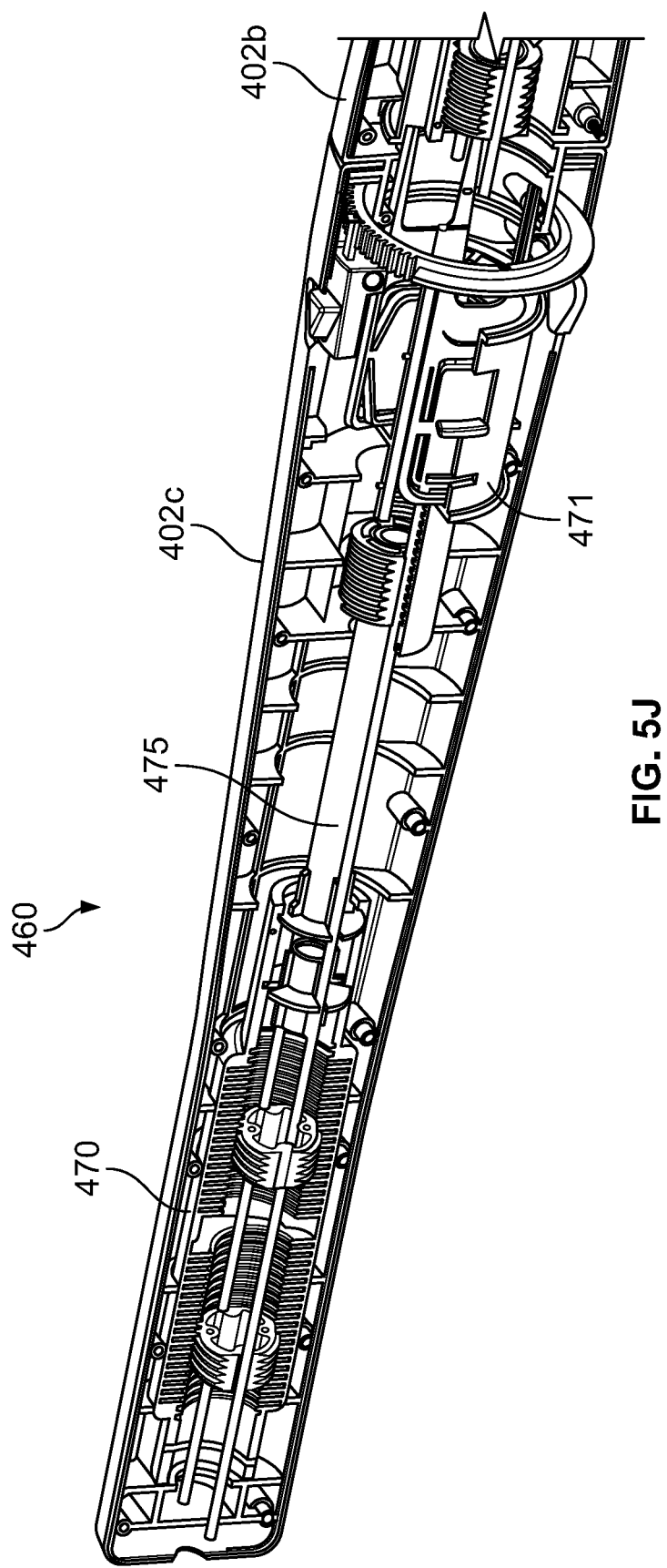
FIG. 5J is a perspective cut-away view of a third portion of the handle of FIG. 5A.

FIG. 5J illustrates third handle portion 460 with portions of third shell 402c omitted to show components inside the third shell. Third handle portion 460 includes a rotation knob 470 coupled to a linear drive knob 471 by a piston 475.

Figure 5K:
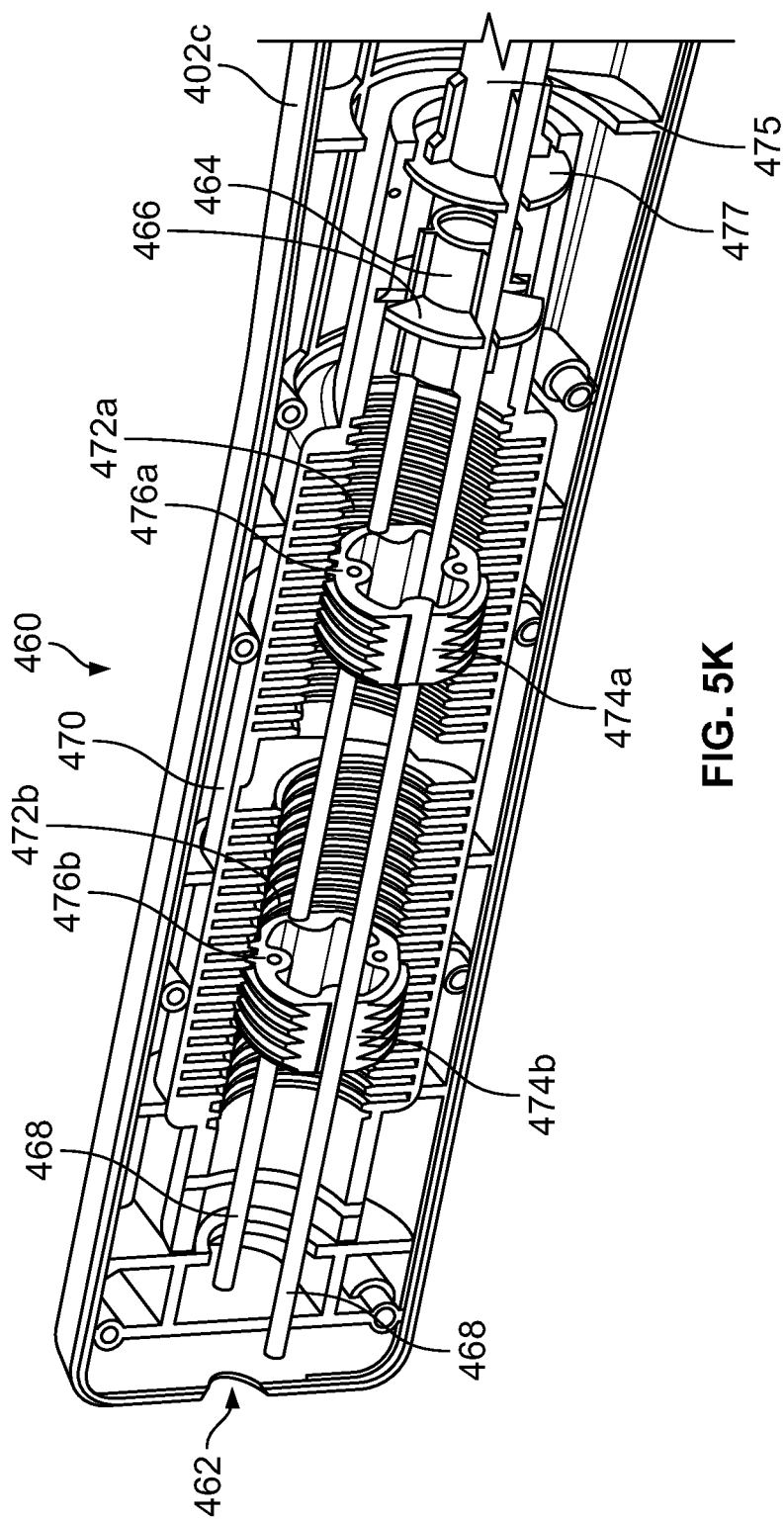
FIG. 5K is an enlarged perspective cut-away view of a rotation knob of the third handle portion of FIG. 5J.

Referring to FIG. 5K, the proximal end of shell 402c may include an opening 462 to allow for fourth sheath 540, fifth sheath 550, and flushing sheath 590 (illustrated in FIG. 5A) to pass into third handle portion 460. However, as noted elsewhere, if additional handle portions are included to help control fourth sheath 540 and/or fifth sheath 550, additional handle portions may be provided proximal of third handle portion 460. Rotation knob 470 is substantially similar to rotation knob 450 and provides similar function, so it is only briefly described. A coupling member 464 is positioned within rotation knob 470 with a flange 466 captured within a groove or slot in the rotation knob to limit translation of the coupling member with respect to the rotation knob. A proximal end of third sheath 530 may be coupled to a distal inner surface of coupling member 464 so that the third sheath is rotationally and translationally fixed to the coupling member. Third sheath 530 may extend from coupling member 464 distally through piston 475, with fourth sheath 540 and fifth sheath 550 extending from within the third sheath through the third coupling member. Flushing sheath 590 may be coupled to a proximal end of coupling member 464, and allow for flushing solution such as saline to be introduced from a hub outside third handle portion 460, the hub being in fluid communication with flushing sheath 590. Rotation knob 470 may include two internally threaded portions 472a, 472b that engage with external threads of drive nuts 474a and 474b, respectively. Preferably, the threads in threaded portion 472a and drive nut 474a are angled in a direction opposite the threads in threaded portion 472b and drive nut 474b so that rotation of knob 470 causes the drive nuts to translate toward or away from one another depending on the direction the knob is rotated. A single pull-wire (not shown) is coupled to through hole 476a of drive nut 474a and another single pull-wire (not shown) is coupled to through hole 476b of drive nut 474b. The two pull-wires extend distally along opposite side walls of third sheath 530. As a user rotates knob 470, drive nuts 474a and 474b move either toward or away from one another, providing for bending of third sheath 530, with the directionality of the bend depending on the directionality of rotation of knob 470. Alignment bars 468 help prevent rotation of certain components, such as drive nuts 474a and 474b, with respect to third shell 402c. It should be understood that the bending of third sheath 530 may not be necessary if the bending of second sheath 520 is sufficient to position the third sheath as desired. In such situations, third handle portion 460 may omit structures directed to the operation of these pull-wires.

Figure 5L:
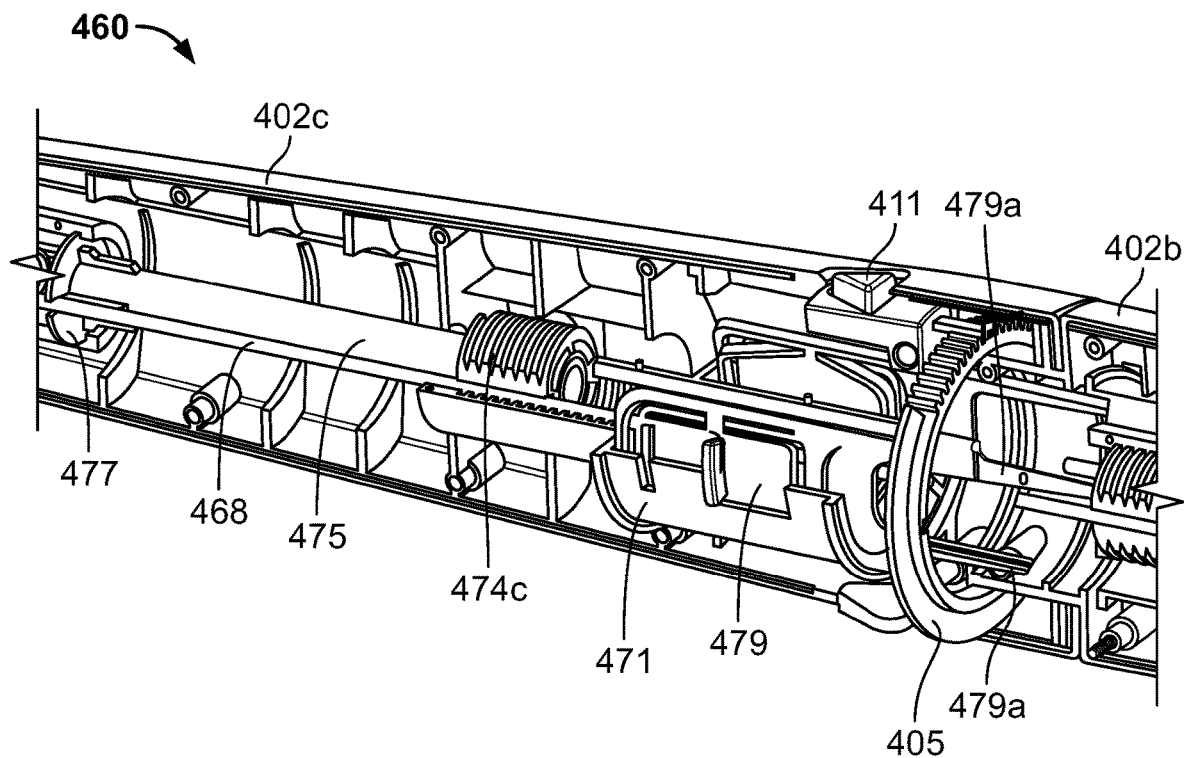
FIG. 5L is an enlarged perspective cut-away view of a linear drive knob of the third handle portion of FIG. 5J.

Referring to FIG. 5L, piston 475 includes a flange 477 engaged within a corresponding groove in rotation knob 470. Piston 475 is substantially the same as piston 455 and provides similar function. A drive nut 474c is rotationally and translationally fixed to an end of piston 475. Drive nut 474c is substantially identical to drive nut 454c, and includes external threads that engage with internal threads of drive knob 471. Rotation of drive knob 471 causes drive nut 474c to translate within third handle portion 460, resulting in a corresponding translation of piston 475 and rotation knob 470. As a result, if a user rotates drive knob 471, third sheath 530 translates with respect to handle 400. In the illustrated embodiment, distal translation of third sheath 530 may result in corresponding translation of fourth sheath 540 and fifth sheath 550, for example due to frictional engagement. However, in other embodiments, one or more additional handle portions may be provided to assist synchronized (or non-synchronized) translation of the fourth sheath 540 and fifth sheath 550 along with third sheath 530.

Figure 5M:
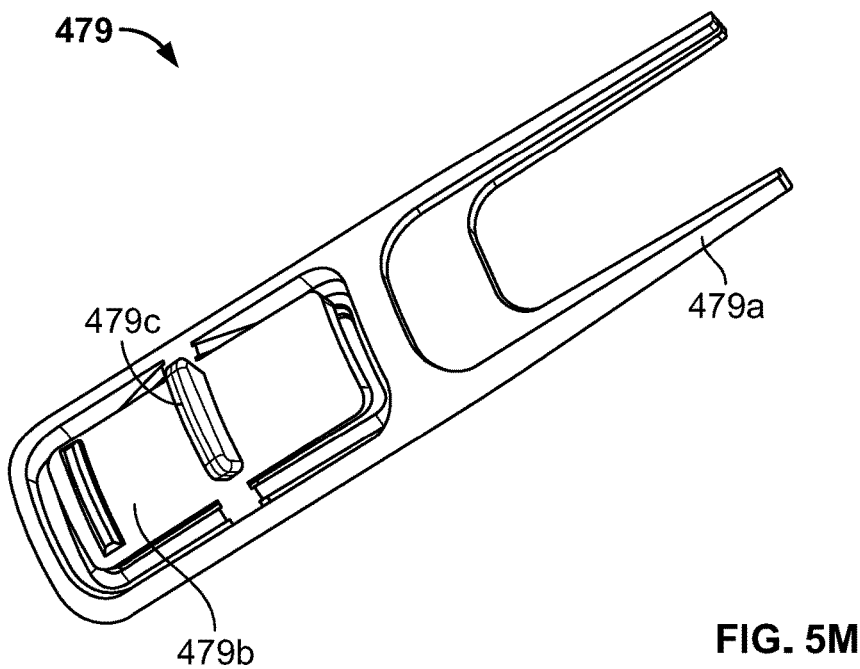
FIG. 5M is a perspective view of a linkage mechanism of the linear drive knob of FIG. 5L.

Linear drive knob 471 may be either rotationally engaged with or rotationally disengaged from linear drive knob 451 via linkage mechanism 479, shown in FIG. 5M. Referring back to FIG. 5I, a pair of linkage mechanisms 479 may be mounted on drive knob 471. Each linkage mechanism 479 may include a pair of prongs 479a extending from a main body 479b toward drive knob 451. A user may manually slide linkage mechanism 479 relative to drive knob 471 by pushing or pulling on a tab 479c projecting from body 479b through a window 471a in drive knob 471. Linkage mechanism 479 will be in the engaged state when tab 479c contacts the distal edge of window 471a, and will be in the disengaged state when tab 479c contacts the proximal edge of window 471a. When linkage mechanism 479 is slid toward the engaged state with drive knob 451, prongs 479a will enter corresponding recesses in drive knob 451. When linkage mechanism 479 is slid to the disengaged state, shown in FIG. 5I, the prongs of 479a of the linkage mechanism will be positioned a spaced distance from drive knob 451. The body 479b of linkage mechanism 479 may include different indicia, one of which at a time will be visible through window 471a to identify whether drive knobs 451 and 471 are in the engaged or disengaged state. Preferably, two linkage mechanisms 479 are provided so that, in the engaged state, a total of four prongs 479a are positioned in recesses in drive knob 451, two prongs on each side of the drive knob. When in the engaged state, rotation of drive knob 451 causes a corresponding rotation of drive knob 471, and vice versa. Thus, in the engaged state, a user may translate second sheath 520 and third sheath 530 in unison by rotating either drive knob 451 or drive knob 471. It should be understood that in another embodiment, linkage mechanism 479 may be reversed in the sense that the linkage mechanism may be mounted on drive knob 451 and prongs 479a may be arranged to extend into corresponding recesses in drive knob 471 to rotationally engage the drive knobs.

FIG. 6A illustrates a distal end of catheter assembly 500 in a delivery condition. FIG. 6B illustrates a cross-section of the distal end of catheter assembly 500 in the delivery condition. The distal end of catheter assembly 500 includes a compartment 560 adapted to receive a prosthetic heart valve similar to prosthetic heart valves 100 or 200 in a radially collapsed condition during delivery of the prosthetic valve to the location of the native mitral valve 26. Third sheath 530 may include a hub 532 attached over its distal end. Hub 532 has a conically tapered recess 534 at its distal end that defines one end of compartment 560. When received within compartment 560, inflow end 110 of prosthetic heart valve 100 may abut the tapered recess 534 of hub 532, and may also in some circumstances extend into the inner diameter of third sheath 530. A retention hub 542 may be coupled to the distal end of fourth sheath 540 near the other end of compartment 560. Retention hub 542 includes a plurality of retainer recesses 544 adapted to receive corresponding retainers 151 of prosthetic heart valve 100.

FIGS. 7A-G illustrate steps for delivering a collapsible prosthetic heart valve, such as prosthetic heart valve 100 or 200, to replace the function of a native mitral valve 26 via a transseptal delivery route. Standard practices may be used to obtain femoral vein access, and a guidewire 70 may be passed from the femoral vein to right atrium 10 through the inferior vena cava 14. A puncture 80 may be made in the septum dividing the right atrium 10 from the left atrium 24, and guidewire 70 may be advanced through the left atrium and native mitral valve 26 into the left ventricle 28. The septal puncture may be made with a needle, with dilators used to increase the size of the septal puncture to allow the delivery system and/or the guidewire to fit through the puncture. With guidewire 70 positioned in the left ventricle 28, the distal end of the fifth sheath 550 of catheter assembly 500 may be fed over the guidewire. It should be understood that, at this point, prosthetic heart valve 100 is already collapsed and positioned within compartment 560 in the delivery condition.

With catheter assembly 500 positioned over guidewire 70, the user may advance the catheter assembly toward the right atrium 10. Rotation knob 430 may be rotated in order to bend first sheath 510 (and thus all other sheaths passing through the first sheath), to assist in traversing the anatomy and to facilitate aligning the first sheath with the puncture 80 in the atrial septum. Further, the user may rotate the first sheath 510 about its axis by rotating handle 400 to help position the distal end of the catheter assembly 500 as desired.

Figure 7A:
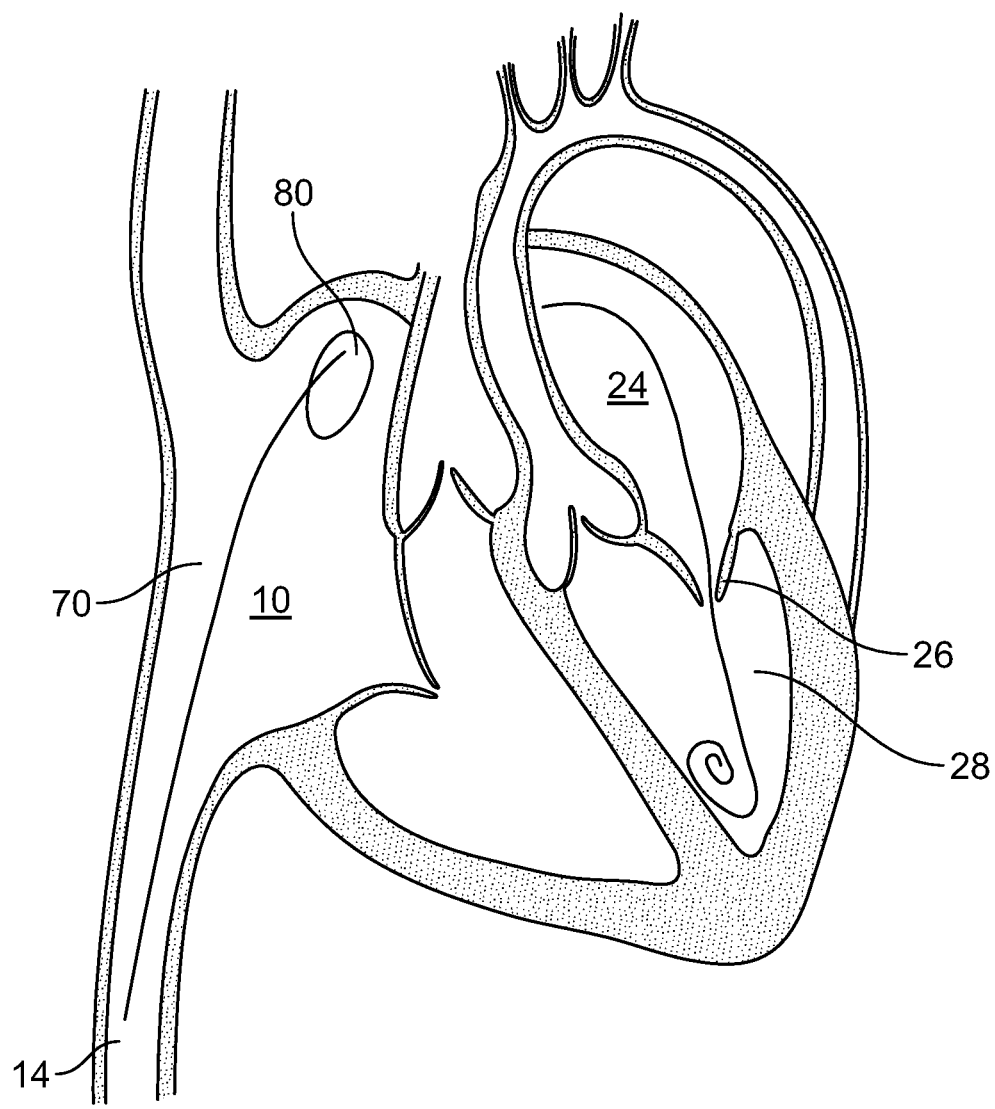
FIGS. 7A-G are schematic views of a transseptal mitral valve delivery procedure.
Figure 7B:
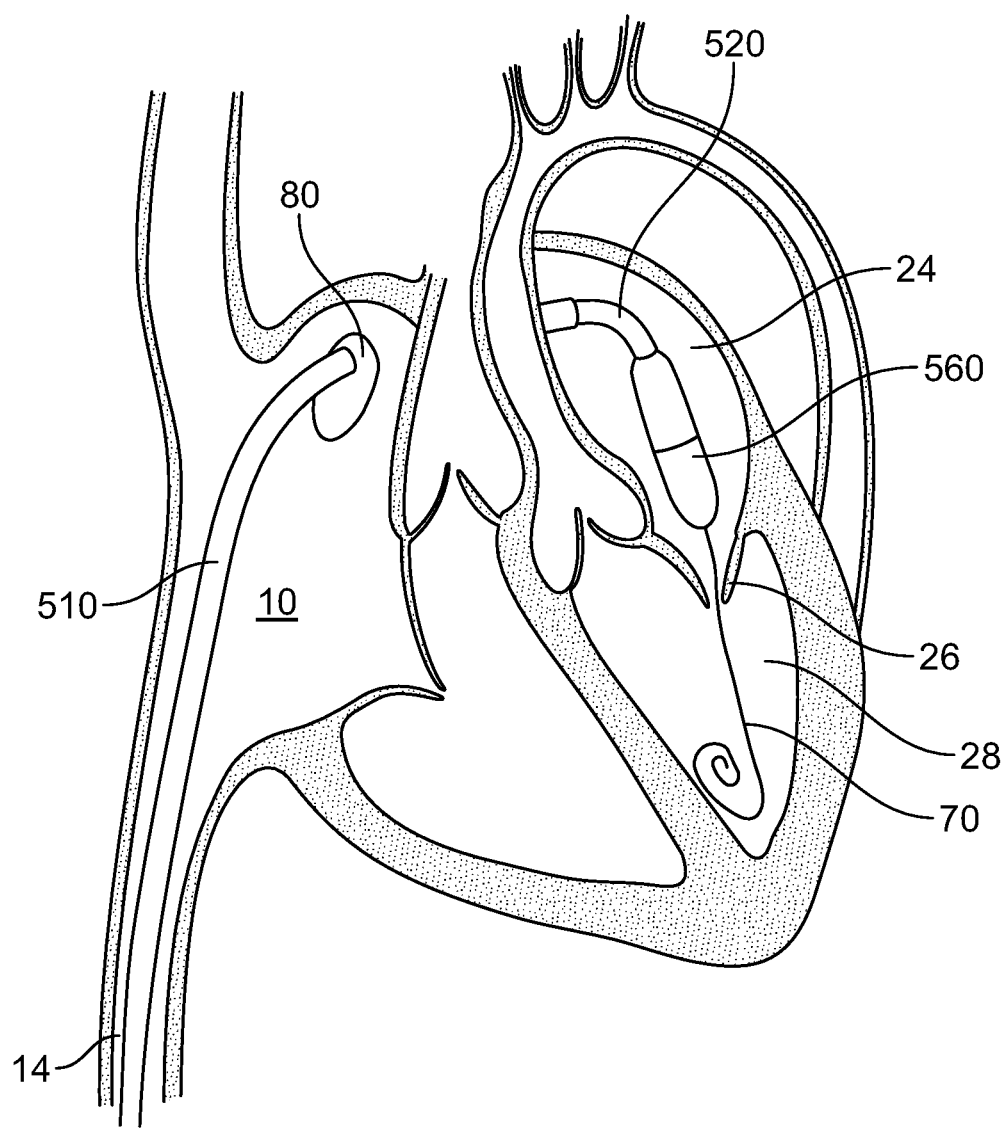

As shown in FIG. 7B, first sheath 510 is advanced through the septal puncture 80 and into the left atrium 24, although in some embodiments the distal end of the first sheath may be positioned within the septal puncture or within the right atrium 10 near the septal puncture. Once the distal end of first sheath 510 is positioned as desired, the user may adjust the position of the distal end of second sheath 520 so that it is substantially coaxial with the annulus of the native mitral valve 26. This may be accomplished by rotating drive knob 451 to advance second sheath 520 toward mitral valve 26. Preferably, drive knob 451 is rotationally engaged with drive knob 471 while advancing second sheath 520 so that third sheath 530 is simultaneously advanced. Further, the user may bend second sheath 520 (and all other sheaths extending within the second sheath) by rotating knob 450. If the user desires to rotate second sheath 520 about its axis, the user may first transition first handle portion 420 to the rotationally disengaged condition with respect to second handle portion 440 by depressing button 410, and may then rotate the second handle portion and third handle portion 460 together about their axes with respect to the first handle portion.

After the distal end of second sheath 520 is suitably aligned with the native mitral valve 26, as shown in FIG. 7B, the user may advance compartment 560 until it is positioned within or beyond the annulus of the native mitral valve. The compartment 560 may be advanced by advancing third sheath 530 relative to the second sheath 520. To accomplish this, the user may transition drive knob 451 to the rotationally disengaged state with respect to drive knob 471 by retracting linkage mechanism 479. With the drive knobs 451 and 471 in the rotationally disengaged state, the user may rotate drive knob 471 to advance third sheath 530 relative to second sheath 520. The user may also bend third sheath 530 as desired by rotating knob 470 to better position compartment 560 relative to the mitral valve annulus.

If prosthetic heart valve 100 includes engaging arms 170 (or other similar engaging arms) to clip over the leaflets of the native mitral valve, it is preferable to properly align the engaging arms with the native mitral valve leaflets before deployment. Thus, prior to initiating deployment of prosthetic heart valve 100 from compartment 560, the user may rotationally disengage second handle portion 440 from third handle portion 460 by depressing button 411, and may rotate the third handle portion about its axis relative to the second handle portion until engaging arms 170 are aligned with the native mitral valve leaflets. Rotation of third sheath 530 may cause corresponding rotation of fourth sheath 540 and fifth sheath 550 through frictional engagement. It should be understood that if pull-wires are included in third sheath 530, it may be desirable to allow for rotation of third sheath 530 relative to fourth sheath 540 and fifth sheath 550, which may be accomplished for example with additional handle portions. However, in the absence of pull-wires in third sheath 530, it may be preferable to ensure that the third sheath 530 is rotationally coupled to the fourth sheath 540 and fifth sheath 550. It should be understood that prosthetic heart valves may not include engaging arms similar to those provided with prosthetic heart valves 100 and 200. In those instances, or in instances in which anchor arms are provided but the orientation of those anchor arms are not important, the rotational position of the prosthetic heart valve may not be critical, and thus third sheath 530 may not need the ability to rotate separately from second sheath 520.

Figure 7C:
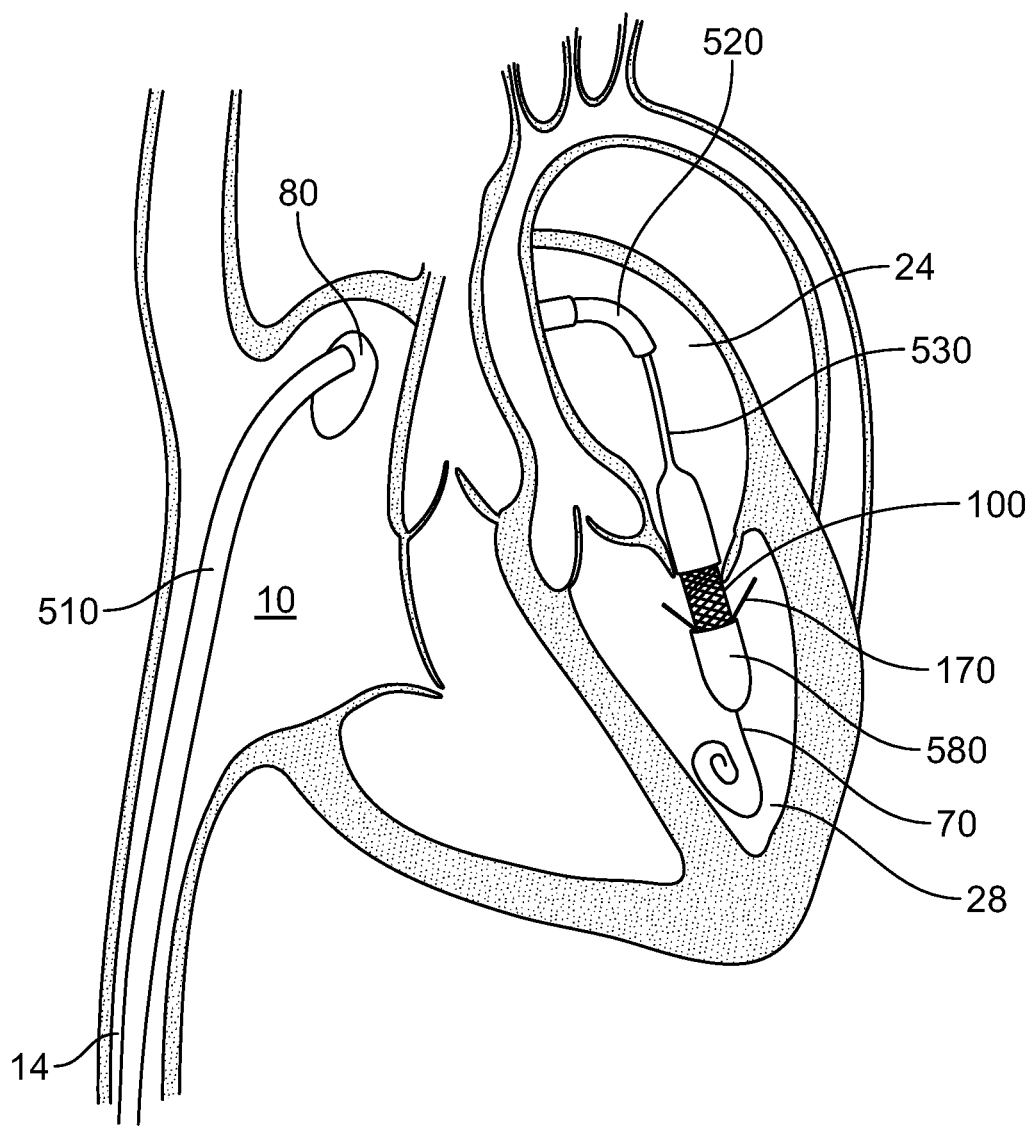

With the engaging arms 170 of prosthetic heart valve 100 properly aligned, the user may initiate deployment of the prosthetic heart valve. As shown in FIG. 7C, the user may advance retaining sheath 580 with respect to third sheath 530 and fourth sheath 540 by manually advancing fifth sheath 550. Although the illustrated embodiment provides for manual translation of fifth sheath 550, in other embodiments additional handle portions may be provided to assist in causing such movements. Since tip 570 is attached to fifth sheath 550 and retaining sheath 580 is attached to the tip, manually advancing the fifth sheath will also advance the retaining sheath. As retaining sheath 580 advances away from hub 532, engaging arms 170 of prosthetic heart valve 100 may expand radially outwardly as shown in FIG. 7C. However, even as engaging arms 170 spring outwardly, the inflow end 110 of prosthetic heart valve 100 remains within the tapered recess 534 of hub 532 and the outflow end 112 remains attached to retaining hub 542 due to retaining sheath 580 keeping the prosthetic heart valve retainers 151 in retainer recesses 544. Engaging arms 170 may include one or more alignments markers, which may be radiopaque, in order to assist in determining the proper positioning of the engaging arms. Although rotation of third handle portion 460 to align engaging arms 170 with the native valve leaflets has been described with prosthetic heart valve 100 retained in the delivery condition, it should be understood that the third handle portion may be rotated additionally or alternatively after the engaging arms have sprung outwardly from the prosthetic heart valve. Further, although FIG. 7C illustrates engaging arms 170 exposed in left ventricle 28, in some situations it may be suitable to expose the engaging arms in left atrium 24 and to then advance the prosthetic heart valve into the left ventricle.

Figure 7D:
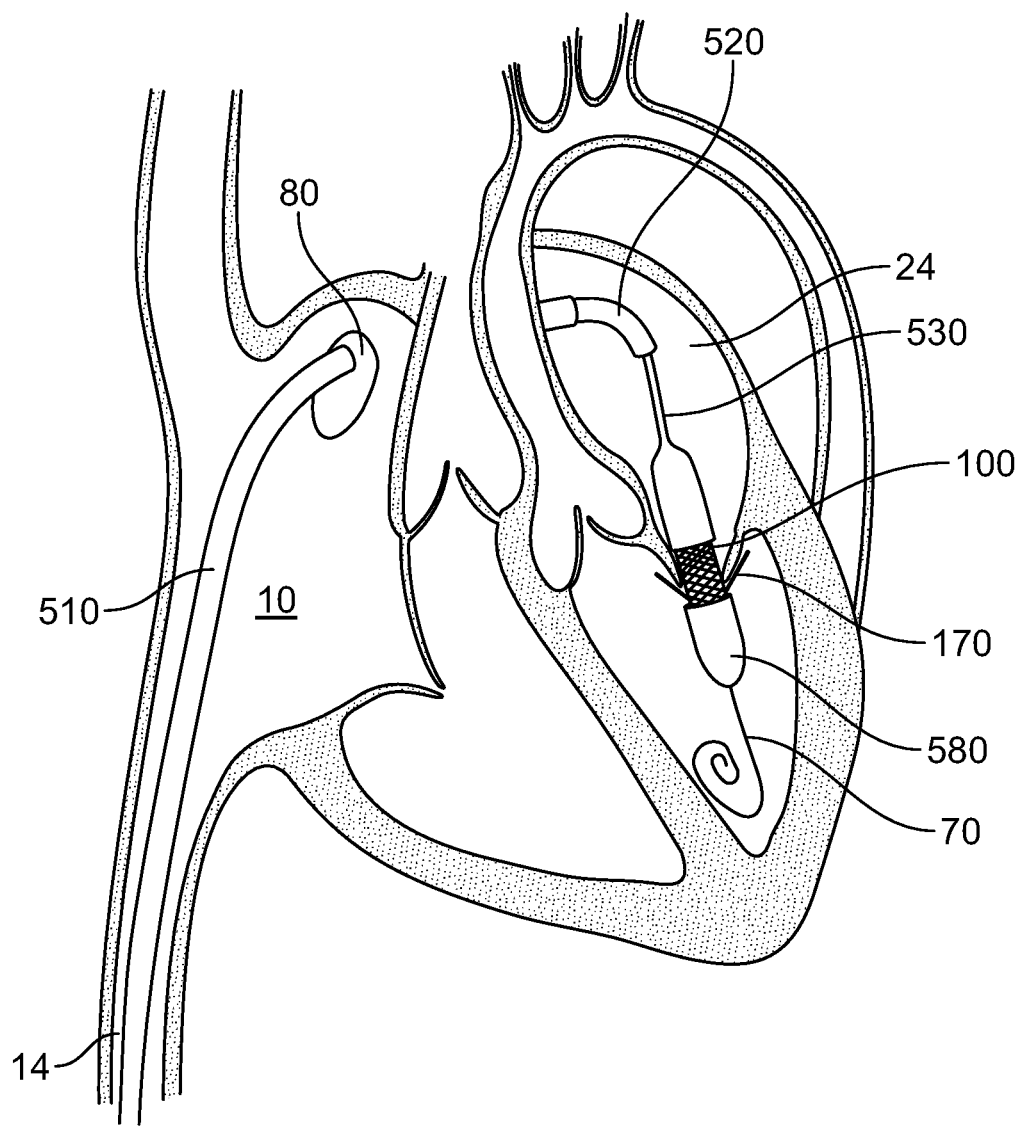

With the engaging arms 170 of prosthetic heart valve 100 positioned within the left ventricle and in a desired rotational position, the user may retract third sheath 530 back into second sheath 520 until the engaging arms engage the native mitral valve leaflets, as shown in FIG. 7D. In order to retract third sheath 530, the user may rotate drive knob 471 in the opposite direction than was used to advance the third sheath, again with drive knobs 451 and 471 rotationally disengaged from one another. The fourth sheath 540 and fifth sheath 550 preferably are retracted along with the third sheath 530, which may be completed manually or through the use of additional handle portions.

Figure 7E:
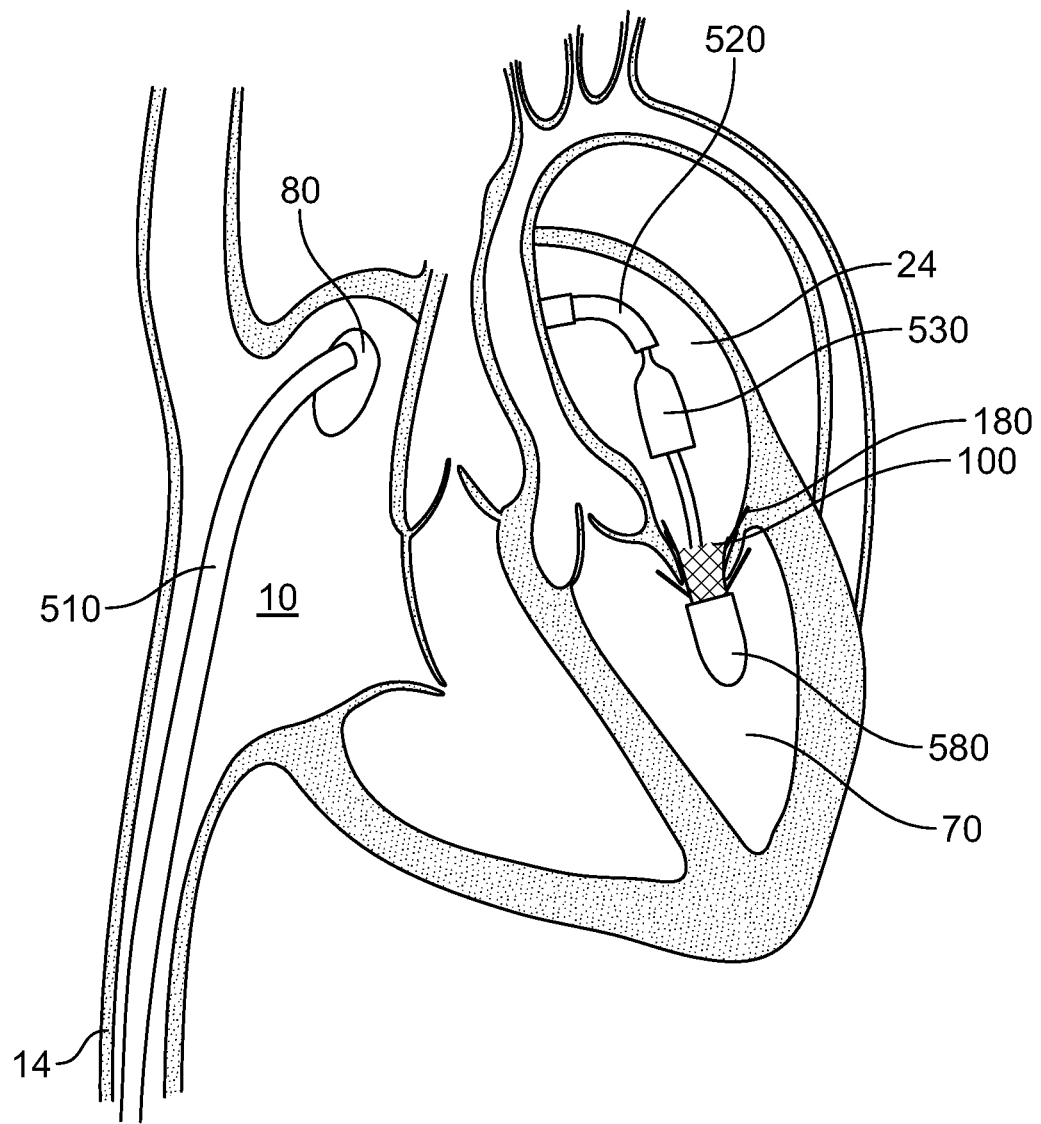
Figure 7F:
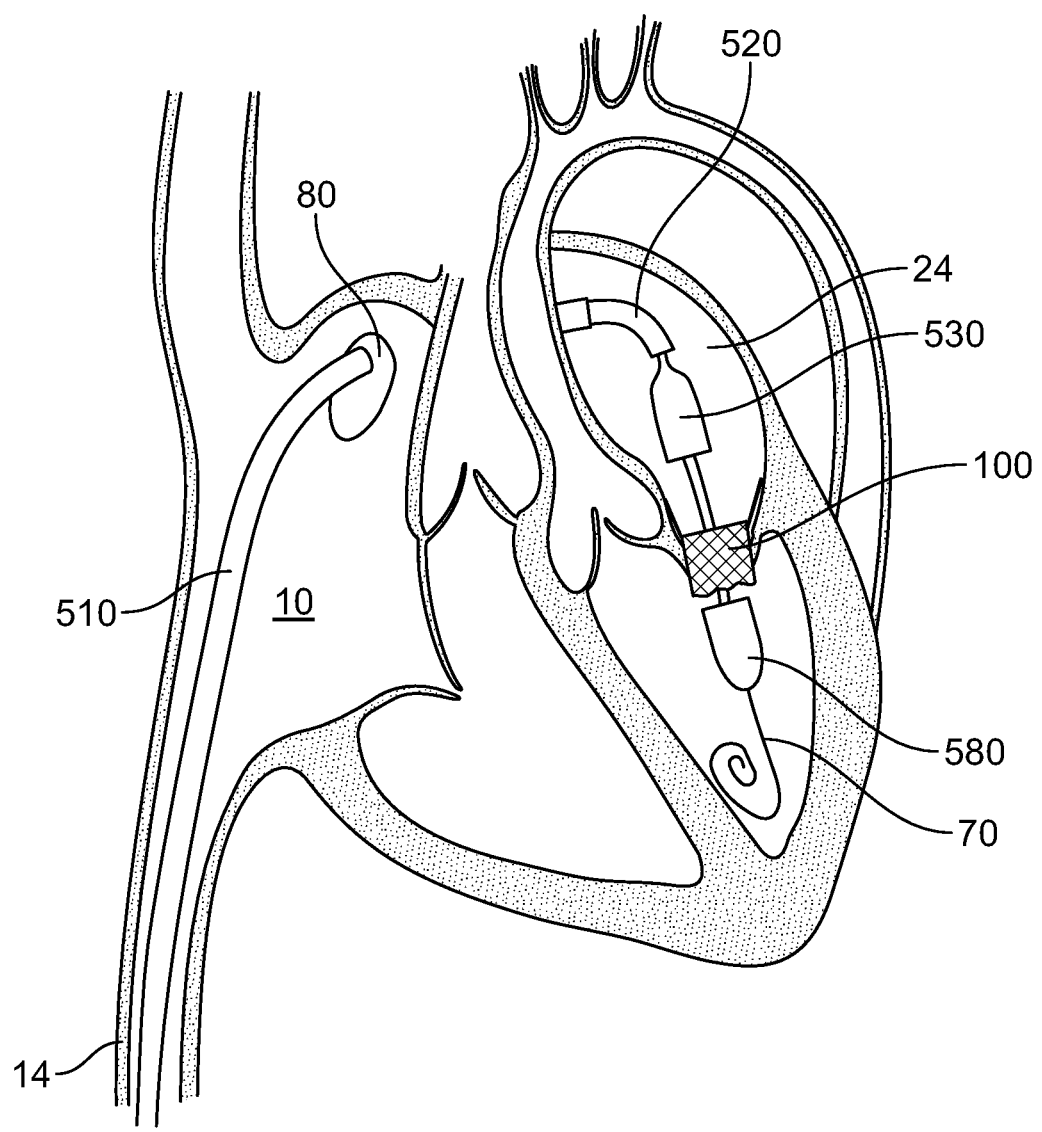

After engaging arms 170 engage the leaflets of native mitral valve 26, the user may fully deploy the inflow end 110 of prosthetic heart valve 100 so that flared section 180 expands and abuts the native mitral valve annulus in left atrium 24. The user may accomplish this by withdrawing third sheath 530 relative to fourth sheath 540 and fifth sheath 550 until the inflow end 110 of prosthetic heart valve 100 is released from the tapered recess 534 of hub 532, as shown in FIG. 7E. The user may then confirm that the prosthetic heart valve 100 is in a desired position. If the prosthetic heart valve 100 is not in a desired position, the user may resheath the prosthetic heart valve because retainers 151 at the outflow end 112 of the prosthetic valve are still captured between the retainer recesses 544 of retention hub 542 and retaining sheath 580. To resheath the prosthetic heart valve 100 at this point, the user may advance third sheath 530, fourth sheath 540 and fifth sheath 550 until engaging arms 170 clear the native mitral valve leaflets, and then retract retaining sheath 580 by retracting fifth sheath 550 relative to fourth sheath 540. Depending on the length of certain components, it may be difficult to fully recapture the entire heart valve 100 after deployment begins. In those scenarios, the engaging arms 170 may still be recaptured after being exposed. The user may then attempt to reposition the prosthetic heart valve. Otherwise, if prosthetic heart valve 100 is suitably positioned, the prosthetic heart valve may be fully released from compartment 560 by continuing to advance fifth sheath 550 relative to third sheath 530 and fourth sheath 540. Advancing fifth sheath 550 will advance tip 570 and retaining sheath 580 relative to retention hub 542, eventually uncovering the retainers 151 of prosthetic heart valve 100 so that they expand out and away from retainer recesses 544, fully releasing the prosthetic heart valve as shown in FIG. 7F.

Figure 7G:
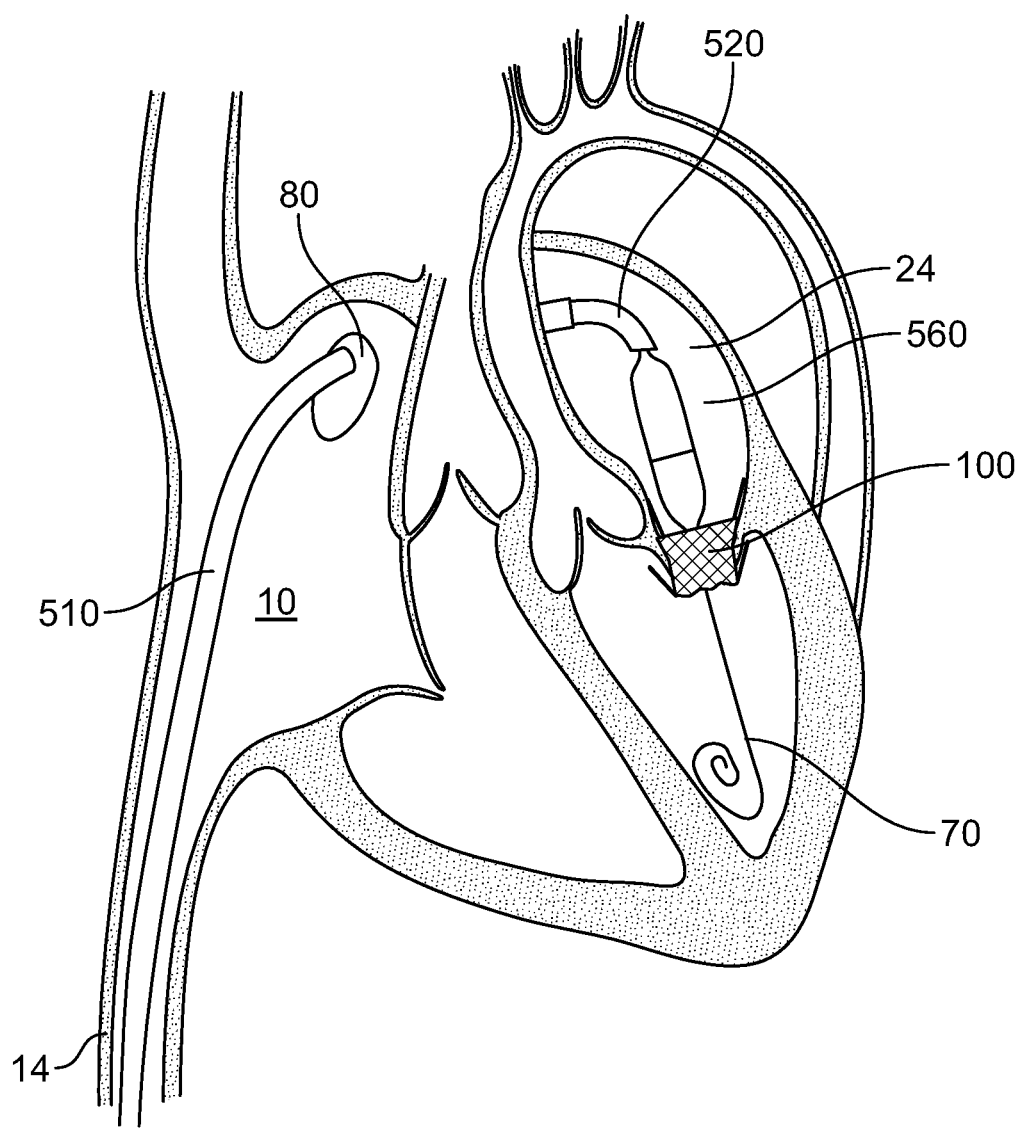

At this point, prosthetic heart valve 100 is fully implanted and delivery device 300 may be removed from the body. In order to remove delivery device 300, the user may retract fifth sheath 550 until retaining sheath 580 passes through prosthetic heart valve 100 and engages hub 532 and compartment 560 is closed. To the extent necessary, any of the bendable sheaths may be bent to properly align the various sheaths during removal, and third sheath 530 may be withdrawn relative to second sheath 520, and second sheath 520 may be withdrawn relative to first sheath 510, until catheter assembly 500 is in a similar condition as it was upon delivery into left atrium 24. With catheter assembly 500 in this condition, as shown in FIG. 7G, the entire catheter assembly may be withdrawn from the body. In some cases, the septal puncture 80 may need to be actively closed, although in other cases the septal puncture may be left unattended and heal without additional intervention.

Although catheter assembly 500, and particularly compartment 560, may be used to deliver and deploy either of prosthetic heart valves 100 or 200, alternate designs of the compartment may be particularly suitable for delivery of an "all-stent" design such as that of prosthetic heart valve 100, or delivery of a "hybrid" stent and braid design such as that of prosthetic heart valve 200.

Figure 8A:
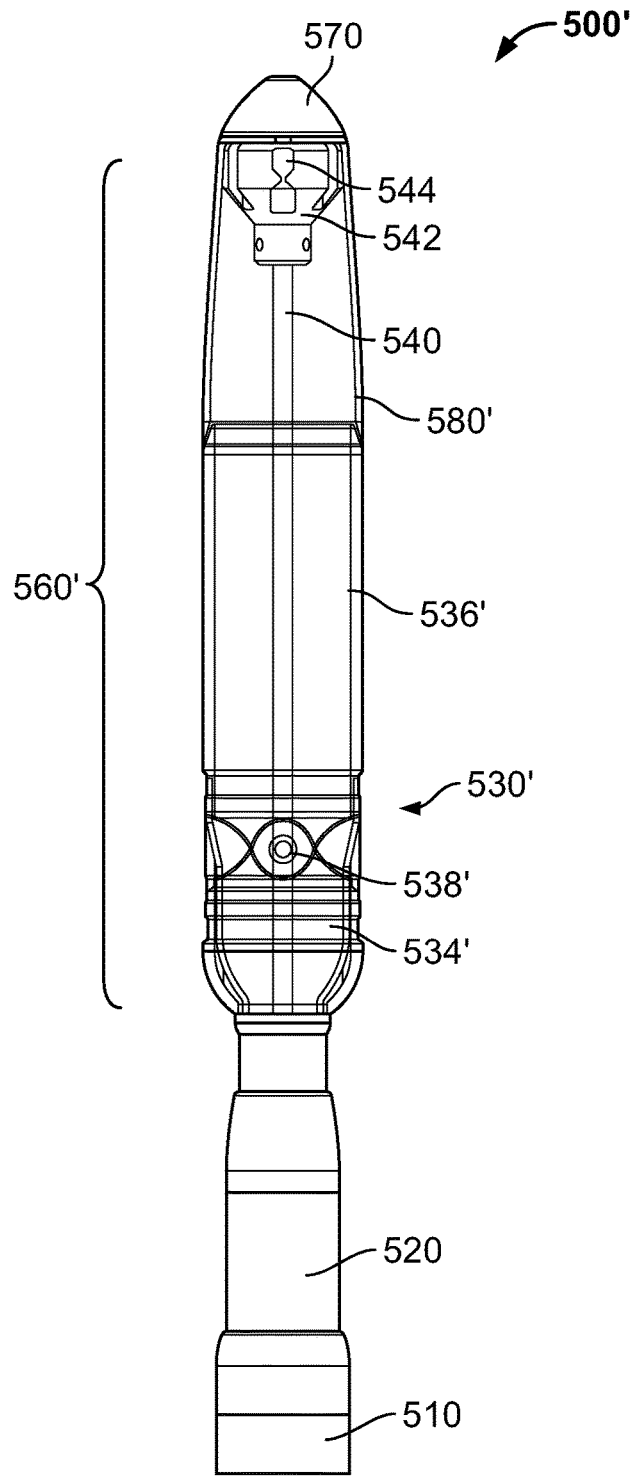
FIG. 8A is a top view of a distal end of a catheter assembly of an alternate mitral valve delivery device.
Figure 8B:
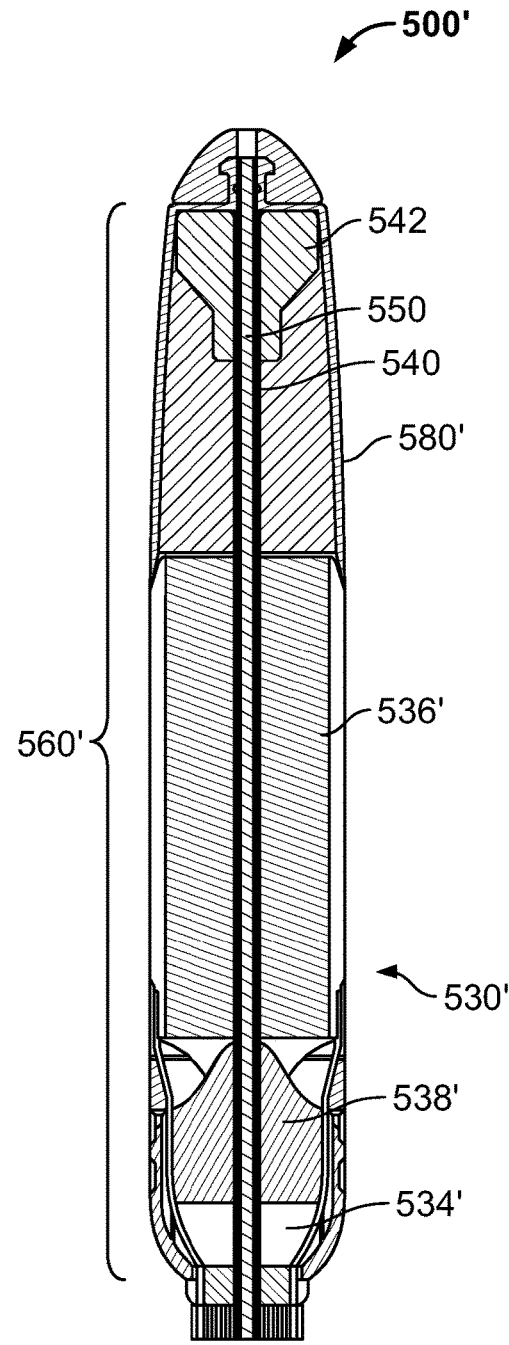
FIG. 8B is a longitudinal cross-section of the distal end of the catheter assembly of FIG. 8A.

FIG. 8A illustrates the distal end of an alternate embodiment of a catheter assembly 500'. FIG. 8B illustrates a cross-section of the compartment 560' of catheter assembly 500'. Catheter assembly 500' may be particularly suited for an all-stent design such as that of prosthetic heart valve 100, although this catheter assembly may still be suited to deliver a hybrid stent design such as that of prosthetic heart valve 200. It should be understood that catheter assembly 500' may be used with handle 400, and many components of catheter assembly 500' may be identical to those of catheter assembly 500. For example, catheter assembly 500' may employ a first sheath 510 and a second sheath 520 that are identical to the identically numbered sheaths of catheter assembly 500. Fourth sheath 540 may extend and couple to a retaining hub 542 including retainer recesses 544, and fifth sheath 550 may extend to atraumatic tip 570, all of which may be similar or identical to the corresponding components in catheter assembly 500. The main differences between catheter assemblies 500 and 500' are compartment 560', retaining sheath 580' (although retaining sheath 580' could be the same as retaining sheath 580 in some embodiments), and third sheath 530'. Due to the limited size of left atrium 24, there is limited space available to reposition compartment 560' once it has passed through septal puncture 80. In order to further assist in positioning prosthetic heart valve 100 to be aligned with the annulus of native mitral valve 26, the distal end of sheath 530' is split between a tapered portion 534' and an articulating portion 536'. Tapered portion 534' may be adapted to contain inlet end 110 of prosthetic heart valve 100, similar to tapered recess 534 of third sheath 530. Articulating portion 536' of third sheath 530' may be pivotally coupled to tapered portion 534' by a pair of pivot pins 538' so that the articulating portion is free to rotate about the pivot pins in a single plane. Retaining sheath 580' may be adapted to close compartment 560' and maintain prosthetic heart valve 100 in a collapsed state. As compartment 560' enters left atrium 24, if tip 570 contacts a wall of the left atrium, articulating portion 536' and retaining sheath 580' will pivot about pivot pins 538' toward alignment with the annulus of native mitral valve 26. The positioning of compartment 560' within the annulus of native mitral valve 26, and the deployment of prosthetic heart valve 100, may otherwise be performed using handle 400 in generally the same manner as described above. An additional difference compared to catheter assembly 500 is that catheter assembly 500' may provide the ability to move the pull wires for third sheath 530' more distally, which may provide for active articulation closer to the distal end of catheter assembly 500'.

Figure 9A:
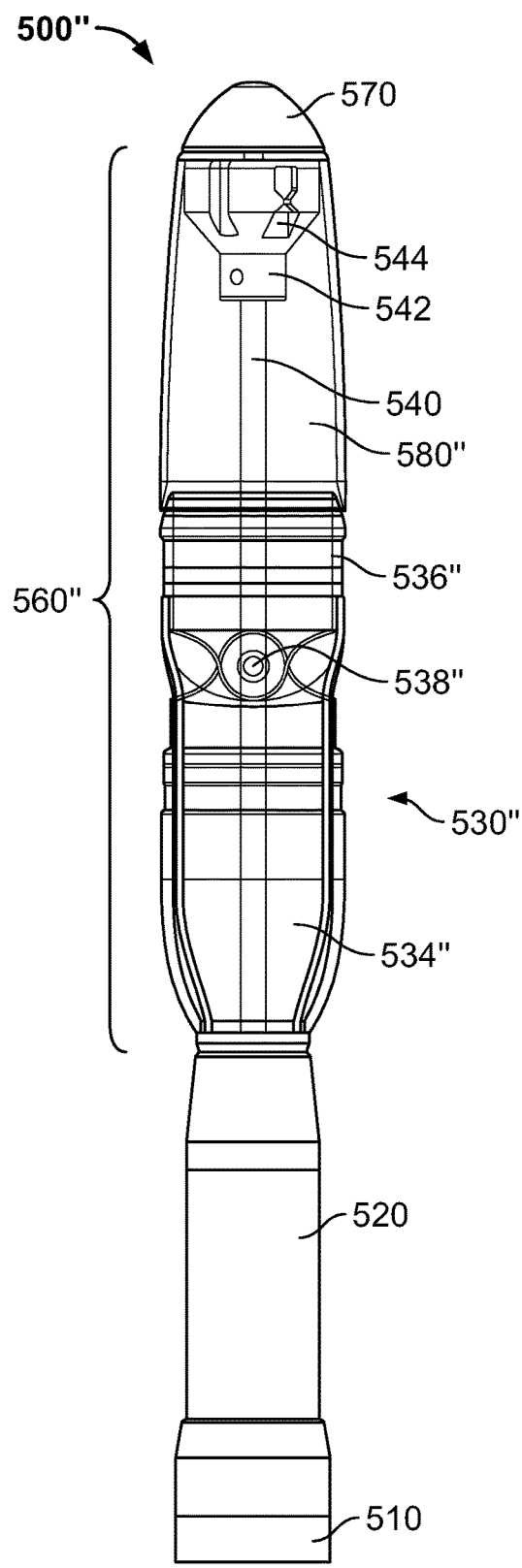
FIG. 9A is a top view a distal end of a catheter assembly of a further mitral valve delivery device.
Figure 9B:
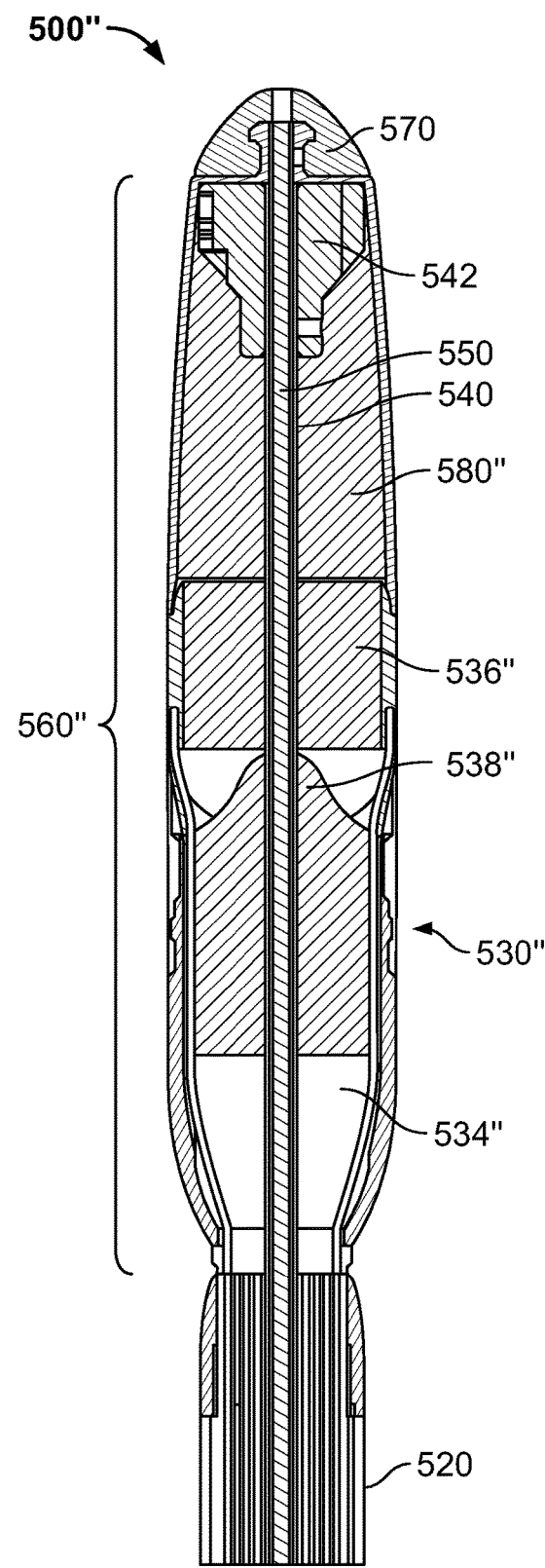
FIG. 9B is a longitudinal cross-section of the distal end of the catheter assembly of FIG. 9A.

FIG. 9A illustrates the distal end of an alternate embodiment of a catheter assembly 500". FIG. 9B illustrates a cross-section of the compartment 560" of catheter assembly 500". Catheter assembly 500" may be particularly suited for a hybrid stent design such as that of prosthetic heart valve 200, although this catheter assembly may still be suited to deliver an all-stent design such as that of prosthetic heart valve 100. It should be understood that catheter assembly 500" may be used with handle 400, and many components of catheter assembly 500" may be identical to those of catheter assembly 500. For example, catheter assembly 500" may employ a first sheath 510 and a second sheath 520 that are identical to the identically numbered sheaths of catheter assembly 500. Fourth sheath 540 may extend and couple to a retaining hub 542 including retainer recesses 544, and fifth sheath 550 may extend to atraumatic tip 570, all of which may be similar or identical to the corresponding structures of catheter assembly 500. Catheter assembly 500" is similar to catheter assembly 500', with the main difference being the positions of pivot pins 538". In particular, third sheath 530" may be split into a first portion including tapered portion 534" and a portion 536" that articulates about pivot pins 538". Compared to catheter assembly 500', the pivot pins 538" of third sheath 530" are positioned closer to tip 570 so that tapered portion 534" is longer and articulating portion 536" is shorter. With this configuration, when prosthetic heart valve 200 is stored in the delivery condition in compartment 560", pivot pins 538" are generally aligned with the transition point between braided flared portion 280 and cylindrical stent portion 282. The flared portion 280 may be particularly flexible and allow articulating portion 536" to pivot relatively easily about pivot pins 538". Further, as noted above, if flared portion 280 is coupled to stent portion 282 by sutures or a similar structure, the flared portion may effectively have a hinged connection to the stent portion, which may further assist in the free articulation of articulation portion 536' relative to tapered portion 534". Otherwise, the delivery of prosthetic heart valve 200 using catheter assembly 500" may be substantially identical to the delivery of prosthetic heart valve 200 using catheter assembly 500.

According to a first aspect of the disclosure, a delivery device for a collapsible prosthetic heart valve, the delivery device comprises:

a handle having a first handle portion, a second handle portion and a third handle portion coupled to one another in series; and a catheter assembly coupled to the handle, the catheter assembly including:

- a first sheath coupled to a first handle portion, the first sheath being rotatable about a longitudinal axis of the first sheath, a distal end of the first sheath being bendable relative to a center portion of the first sheath;
- a second sheath coupled to the second handle portion and extending through an interior of the first sheath, the second sheath being rotatable about a longitudinal axis of the second sheath and relative to the first sheath and being translatable relative to the first sheath, a distal end of the second sheath being bendable relative to a center portion of the second sheath;
- a third sheath coupled to the third handle portion and extending through an interior of the second sheath and the interior of the first sheath, the third sheath being translatable relative to the second sheath; and
- a compartment for receiving the prosthetic heart valve in a collapsed condition, the compartment being operably coupled to the third sheath; and/or the handle has a first state in which the first handle portion is not rotatable relative to the second handle portion, and a second state in which the first handle portion is rotatable relative to the second handle portion; and/or a pawl of the second handle portion engages a toothed ring of the first handle portion in the first state of the handle; and/or the pawl is biased into engagement with the toothed ring in the absence of a force applied to the pawl; and/or in the second state of the handle, the first handle portion has a range of rotation of about 180 degrees relative to the second handle portion; and/or a pawl of the second handle portion engages a toothed ring of the first handle portion in the first state of the handle, and the toothed ring includes a plurality of stops limiting the range of rotation; and/or the handle has a third state in which the second handle portion is not rotatable relative to the third handle portion, and a fourth state in which the second handle portion is rotatable relative to the third handle portion; and/or a pawl of the third handle portion engages a toothed ring of the second handle portion in the third state of the handle; and/or the pawl is biased into engagement with the toothed ring in the absence of a force applied to the pawl; and/or in the fourth state of the handle, the second handle portion has a range of rotation of about 90 degrees relative to the third handle portion; and/or a pawl of the third handle portion engages a toothed ring of the second handle portion in the third state of the handle, and the toothed ring includes a plurality of stops limiting the range of rotation; and/or the second handle portion includes a first linear drive mechanism and actuation of the first linear drive mechanism translates the second sheath relative to the first sheath; and/or the third handle portion includes a second linear drive mechanism and actuation of the second linear drive mechanism translates the third sheath relative to the second sheath; and/or the handle has a rotationally engaged state in which actuation of one of the first linear drive mechanism and the second linear drive mechanism actuates the other of the first linear drive mechanism and the second linear drive mechanism whereby the second sheath and the third sheath translate together relative to the first sheath, and the handle has a rotationally disengaged state in which actuation of one of the first linear drive mechanism and the second linear drive mechanism does not actuate the other of the first linear drive mechanism and the second linear drive mechanism whereby the second sheath translates relative to the first sheath independently of the third sheath; and/or a linkage mechanism coupled to one of the first linear drive mechanism and the second linear drive mechanism, the first linear drive mechanism transitioning from the rotationally disengaged state to the rotationally engaged state when the linkage mechanism is operably coupled to both the first linear drive mechanism and the second linear drive mechanism; and/or a fourth sheath extending through the handle and through an interior of the third sheath, the fourth sheath being translatable relative to the third sheath; and/or a fifth sheath extending through the handle and through an interior of the fourth sheath, the fifth sheath being translatable relative to the fourth sheath and terminating in a tip; and/or a retaining sheath translationally fixed to the tip, the retaining sheath defining an outer periphery of the compartment; and/or a first hub coupled to a distal end of the third sheath and a second hub coupled to the distal end of the fourth sheath, the first hub and the second hub being adapted to support ends of the prosthetic heart valve in the collapsed condition.

According to a second aspect of the disclosure, a method of replacing a native mitral valve of a patient comprises:

advancing a delivery device to a right atrium of the patient, the delivery device having a first sheath, a second sheath translatable relative to the first sheath, a compartment having a closed condition and an open condition and being translatable relative to the first sheath and the second sheath, and a collapsible prosthetic heart valve stored in a collapsed condition within the compartment in the closed condition;

advancing the first sheath toward an opening in a septum wall dividing a left atrium of the patient from the right atrium of the patient;

passing the compartment through the opening in the septum wall;

translating the second sheath relative to the first sheath toward the native mitral valve;

bending a distal end of the second sheath to align the distal end of the second sheath with an annulus of the native mitral valve;

translating the compartment relative to the second sheath toward the native mitral valve; and placing the compartment in the open condition and deploying the prosthetic heart valve into the annulus of the native mitral valve so that the prosthetic heart valve transitions to an expanded condition; and/or the compartment is operably connected to a third sheath and the step of translating the compartment includes translating the third sheath relative to the second sheath; and/or the delivery device further includes another sheath and a retaining sheath operably coupled to the another sheath, the method further comprising translating the another sheath relative to the third sheath to translate the retaining sheath, whereby translation of the retaining sheath causes the compartment to move from the closed condition to a partially open condition; and/or the step of translating the retaining sheath relative to the compartment includes allowing anchor features of the prosthetic heart valve to transition radially outward of the compartment; and/or determining whether the transitioned anchor features align with leaflets of the native mitral valve; and/or rotating the third sheath about a longitudinal axis of the third sheath to reposition the anchor features if it is determined that the transitioned anchor features do not align with the leaflets of the native mitral valve; and/or moving the third sheath and the another sheath away from the annulus of the native mitral valve until the anchor features engage leaflets of the native mitral valve; and/or the delivery device further includes a fourth sheath, the method further comprising translating the fourth sheath relative to the third sheath to release a first end of the prosthetic heart valve from the compartment while a second end of the prosthetic heart valve remains in the compartment; and/or further translating the another sheath relative to the third sheath to translate the retaining sheath relative to the compartment, whereby the compartment is moved to the open condition to release the second end of the prosthetic heart valve from the compartment; and/or retracting the another sheath and the fourth sheath relative to the third sheath to retract the retaining sheath through an interior of the deployed prosthetic heart valve to move the compartment to the closed condition.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A delivery device for a collapsible prosthetic heart valve, the delivery device comprising:
   a handle having a first handle portion, a second handle portion and a third handle portion coupled to one another in series; and
   a catheter assembly coupled to the handle, the catheter assembly including:
      a first sheath coupled to a first handle portion, the first sheath being rotatable about a longitudinal axis of the first sheath, a distal end of the first sheath being bendable relative to a center portion of the first sheath;
      a second sheath coupled to the second handle portion and extending through an interior of the first sheath, the second sheath being rotatable about a longitudinal axis of the second sheath and relative to the first sheath and being translatable relative to the first sheath, a distal end of the second sheath being bendable relative to a center portion of the second sheath;
      a third sheath coupled to the third handle portion and extending through an interior of the second sheath and the interior of the first sheath, the third sheath being translatable relative to the second sheath; and a compartment for receiving the prosthetic heart valve in a collapsed condition, the compartment being operably coupled to the third sheath,
wherein the handle has a first state in which the first handle portion is not rotatable relative to the second handle portion, and a second state in which the first handle portion is rotatable relative to the second handle portion.

2. The delivery device of claim 1, wherein a pawl of the second handle portion engages a toothed ring of the first handle portion in the first state of the handle.

3. The delivery device of claim 2, wherein the pawl is biased into engagement with the toothed ring in the absence of a force applied to the pawl.

4. The delivery device of claim 1, wherein in the second state of the handle, the first handle portion has a range of rotation of about 180 degrees relative to the second handle portion.

5. The delivery device of claim 4, wherein a pawl of the second handle portion engages a toothed ring of the first handle portion in the first state of the handle, and the toothed ring includes a plurality of stops limiting the range of rotation.

6. The delivery device of claim 1, wherein the handle has a third state in which the second handle portion is not rotatable relative to the third handle portion, and a fourth state in which the second handle portion is rotatable relative to the third handle portion.

7. The delivery device of claim 6, wherein a pawl of the third handle portion engages a toothed ring of the second handle portion in the third state of the handle.

8. The delivery device of claim 7, wherein the pawl is biased into engagement with the toothed ring in the absence of a force applied to the pawl.

9. The delivery device of claim 6, wherein in the fourth state of the handle, the second handle portion has a range of rotation of about 90 degrees relative to the third handle portion.

10. The delivery device of claim 9, wherein a pawl of the third handle portion engages a toothed ring of the second handle portion in the third state of the handle, and the toothed ring includes a plurality of stops limiting the range of rotation.

11. The delivery device of claim 6, wherein the second handle portion includes a first linear drive mechanism and actuation of the first linear drive mechanism translates the second sheath relative to the first sheath.

12. The delivery device of claim 11, wherein the third handle portion includes a second linear drive mechanism and actuation of the second linear drive mechanism translates the third sheath relative to the second sheath.

13. The delivery device of claim 12, wherein the handle has a rotationally engaged state in which actuation of one of the first linear drive mechanism and the second linear drive mechanism actuates the other of the first linear drive mechanism and the second linear drive mechanism whereby the second sheath and the third sheath translate together relative to the first sheath, and the handle has a rotationally disengaged state in which actuation of one of the first linear drive mechanism and the second linear drive mechanism does not actuate the other of the first linear drive mechanism and the second linear drive mechanism whereby the second sheath translates relative to the first sheath independently of the third sheath.

14. The delivery device of claim 13, further comprising a linkage mechanism coupled to one of the first linear drive mechanism and the second linear drive mechanism, the first linear drive mechanism transitioning from the rotationally disengaged state to the rotationally engaged state when the linkage mechanism is operably coupled to both the first linear drive mechanism and the second linear drive mechanism.

15. The delivery device of claim 1, further comprising a fourth sheath extending through the handle and through an interior of the third sheath, the fourth sheath being translatable relative to the third sheath.

16. The delivery device of claim 15, further comprising a fifth sheath extending through the handle and through an interior of the fourth sheath, the fifth sheath being translatable relative to the fourth sheath and terminating in a tip.

17. The delivery device of claim 16, further comprising a retaining sheath translationally fixed to the tip, the retaining sheath defining an outer periphery of the compartment.

18. The delivery device of claim 17, further comprising a first hub coupled to a distal end of the third sheath and a second hub coupled to the distal end of the fourth sheath, the first hub and the second hub being adapted to support ends of the prosthetic heart valve in the collapsed condition.

* * * * *